United States Patent [19]

Koike et al.

[11] Patent Number: 5,065,629

[45] Date of Patent: Nov. 19, 1991

[54] ULTRASONIC INSECTION APPARATUS

[75] Inventors: Mitsuhiro Koike; Shusou Wadaka, both of Kanagawa, Japan

[73] Assignee: Mitsubishi Denki Kabushiki Kaisha, Tokyo, Japan

[21] Appl. No.: 595,610

[22] Filed: Oct. 11, 1990

[30] Foreign Application Priority Data

Oct. 25, 1989 [JP] Japan .................................. 1-277863

[51] Int. Cl.$^5$ ..................... G01N 29/22; G06F 15/336
[52] U.S. Cl. ......................................... 73/602; 73/625; 73/642; 364/728.07; 364/821; 367/100; 367/905
[58] Field of Search ................. 73/602, 631, 642, 625; 364/728.07, 728.03, 507, 508, 496, 497, 819, 821; 367/100, 905

[56] References Cited

U.S. PATENT DOCUMENTS

| 3,681,579 | 8/1972 | Scheitzer | 364/728.07 |
| 4,156,876 | 5/1979 | Debuisser | 364/728.07 |
| 4,245,326 | 1/1981 | Gutleber | 364/728.07 |

OTHER PUBLICATIONS

"Time gain control in spread ultrasound", by B. B. Lee and E. S. Furgason, Ultrasonics, vol. 18, No. 3 (May 1980), pp. 136–137.
"An Evaluation of Ultrasound NDE Correlation Flaw Detection Systems", by Brian B. Lee and Eric S. Furgason, IEEE Transactions on Sonics and Ultrasonics, vol. SU-29, No. 6, Nov. 1982, pp. 359–369.
"High-Speed Digital Golay Code Flaw Detection System", by B. B. Lee and E. S. Furgason, Ultrasonic Symposium (1981), IEEE, pp. 888–891.
"High-Speed Digital Golay Code Flaw Detection System", by B. B. Lee and E. S. Furgason, Ultrasonics (Jul. 1983), pp. 153–161.
"Complementary Series", by Marcel J. E. Golay; IRE Transactions on Information Theory, Apr. 1961, pp. 82–87.
"Ultrasonic Testing Technology", by Inc. Association, Nihon Nohritsu Kyokai, Feb. 25, 1980, pp. 177–181 and 296–298.
"Coding Theory", Published by Shokodo, Jun. 30, 1989, pp. 488–490.
"Piezoelectric Multilayer Transducers for Ultrasonic Pulse Compression", by K. M. Sung: Ultrasonics, vol. 22, Mar. 1984, Guildford GB, pp. 61–68.
"Barker–codierte Mehrschichtwandler aus Polyvinylidenfluorid für den Impuls–Echo-Betrieb mit Ultraschall", by Von M. Platte, Acustica Internationale Akustische Zeitschrift, vol. 56, Sep. 1984, Stuttgart, DE, pp. 29–33.

Primary Examiner—Hezron E. Williams
Assistant Examiner—Rose M. Finley
Attorney, Agent, or Firm—Wolf, Greenfield & Sacks

[57] ABSTRACT

An ultrasonic flaw inspecting apparatus is provided in which the transmission signals comprising N number of the binary code sequences having sharp autocorrelation functions are input to an object to be inspected by a single transducer for transmission and the reflected signals are received by N number of transducers for reception. The N number of transducers for reception are connected and placed over each other so that the direction of respective polarization is inverted in terms of the time order of the binary code of the sequence.

5 Claims, 22 Drawing Sheets

Fig. 2(a)
(PRIOR ART)
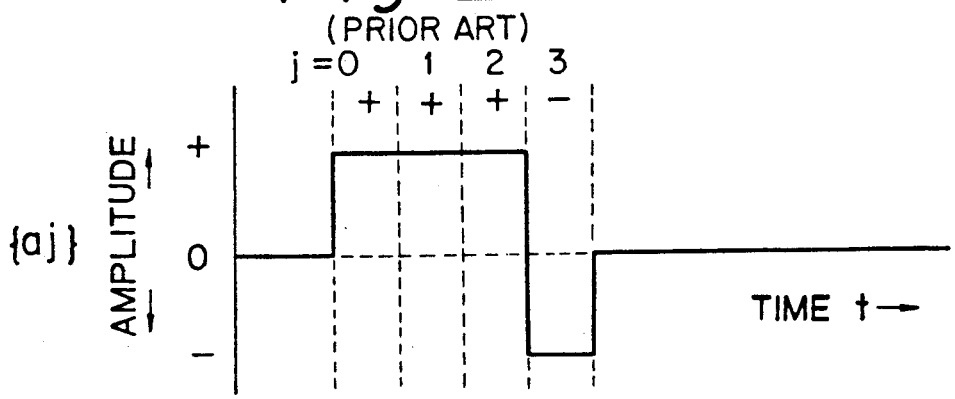
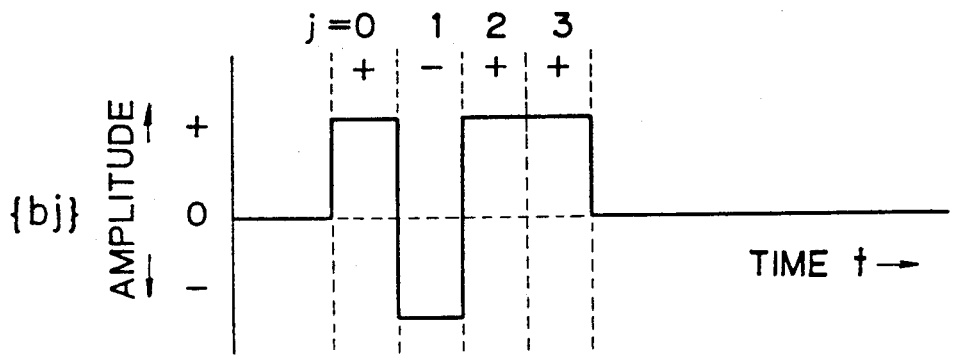
Fig. 2(b)
(PRIOR ART)
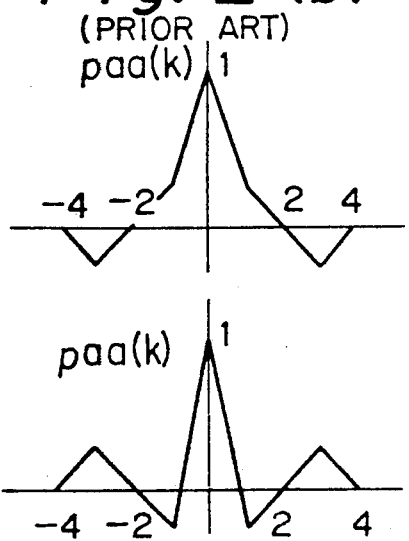
Fig. 2(c)
(PRIOR ART)
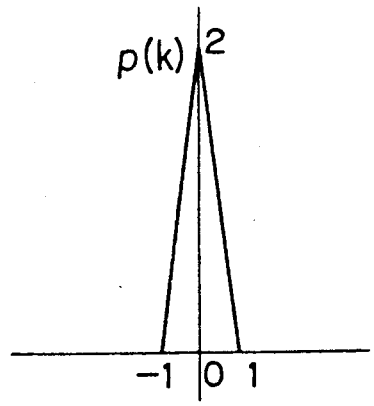

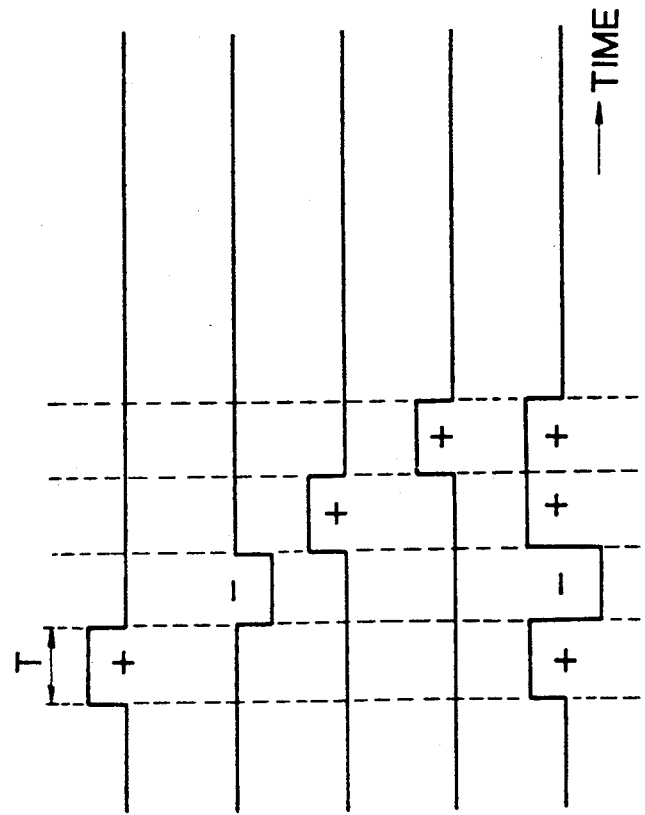
Fig. 7(a)(1) TRANSDUCER 1 FOR TRANSMISSION (PRIOR ART)
Fig. 7(a)(2) TRANSDUCER 2 FOR TRANSMISSION (PRIOR ART)
Fig. 7(a)(3) TRANSDUCER 3 FOR TRANSMISSION (PRIOR ART)
Fig. 7(a)(4) TRANSDUCER 4 FOR TRANSMISSION (PRIOR ART)
Fig. 7(a)(5) COMPREHENSIVE WAVE FORM FOR RECEPTION (PRIOR ART)

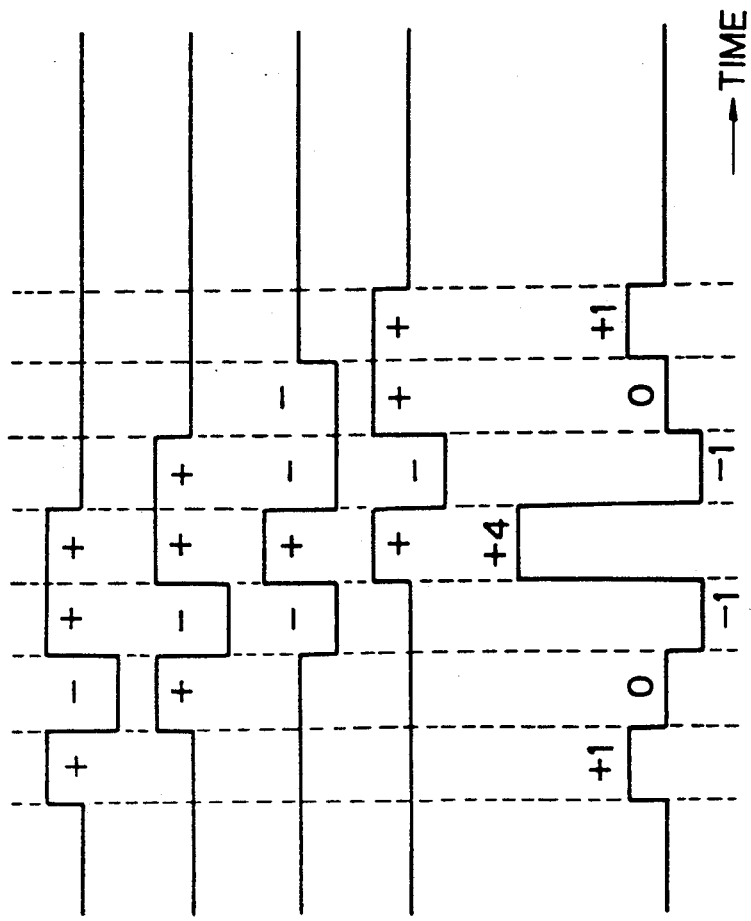
Fig. 7(b)(1) TRANSDUCER 1 FOR RECEPTION (PRIOR ART)
Fig. 7(b)(2) TRANSDUCER 2 FOR RECEPTION (PRIOR ART)
Fig. 7(b)(3) TRANSDUCER 3 FOR RECEPTION (PRIOR ART)
Fig. 7(b)(4) TRANSDUCER 4 FOR RECEPTION (PRIOR ART)
Fig. 7(b)(5) COMPREHENSIVE WAVE FORM FOR RECEPTION (PRIOR ART)

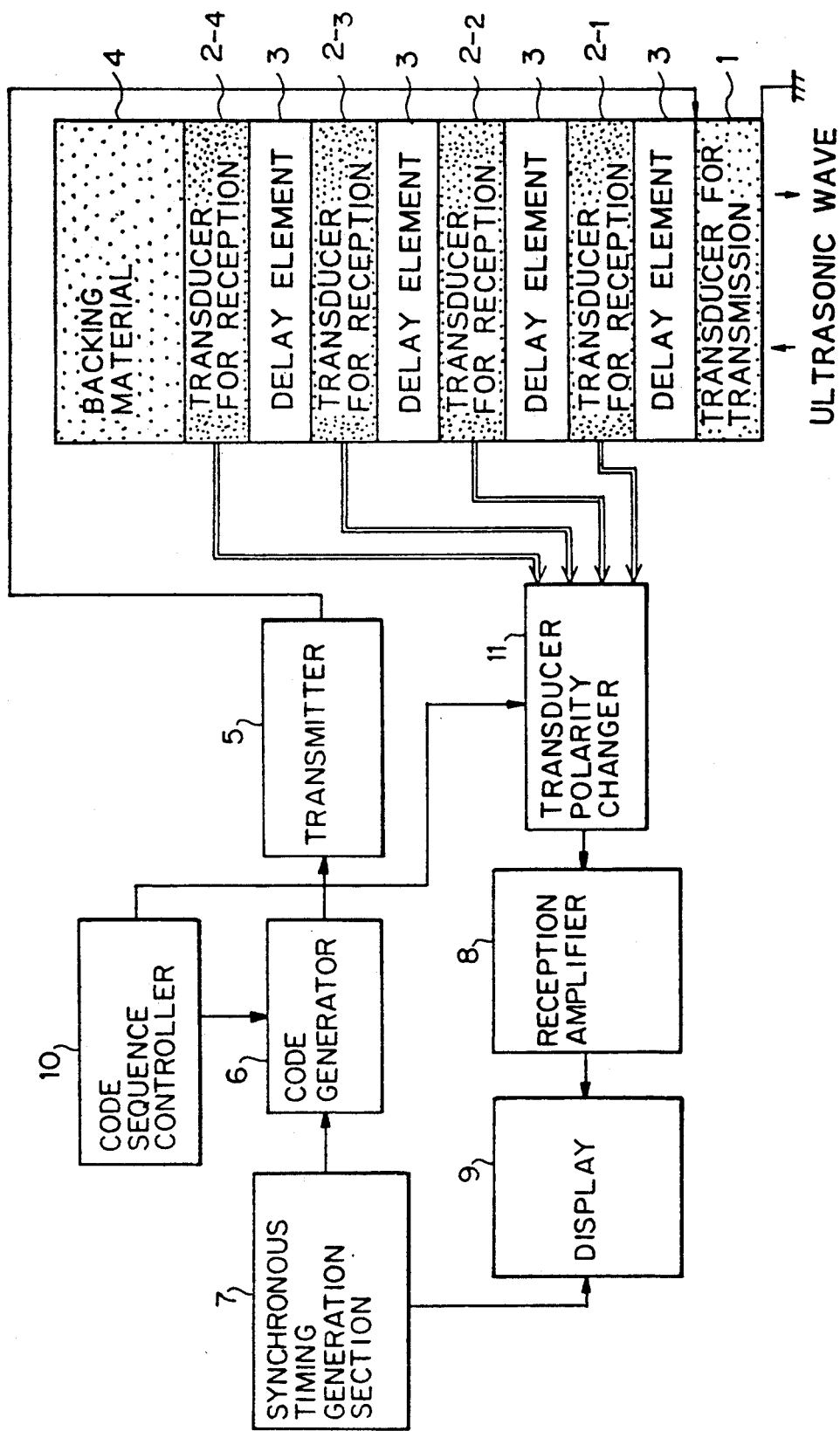

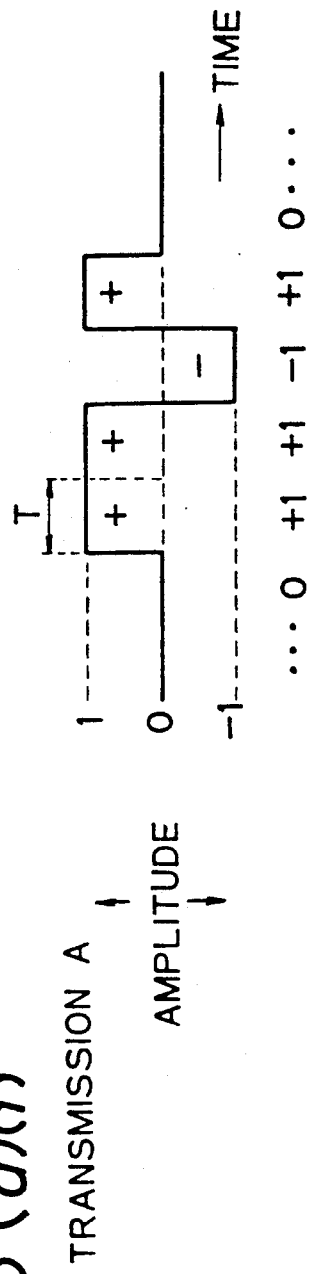
Fig.15(a)(1) TRANSMISSION A
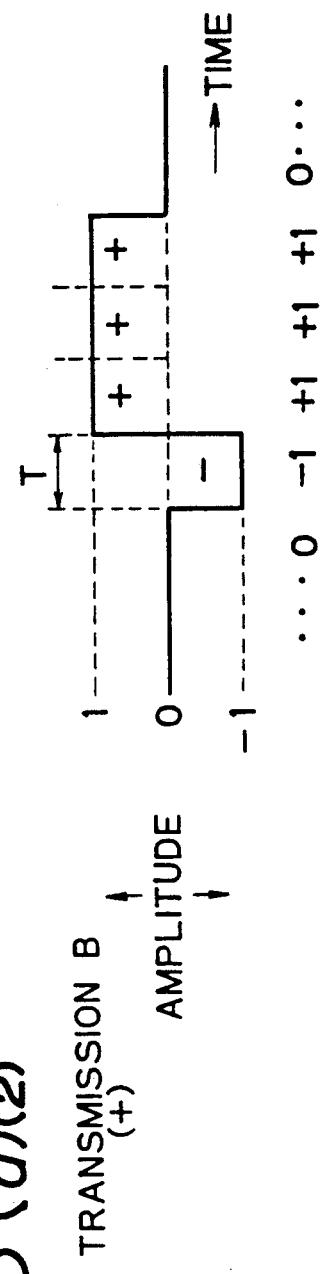
Fig.15(a)(2) TRANSMISSION B (+)

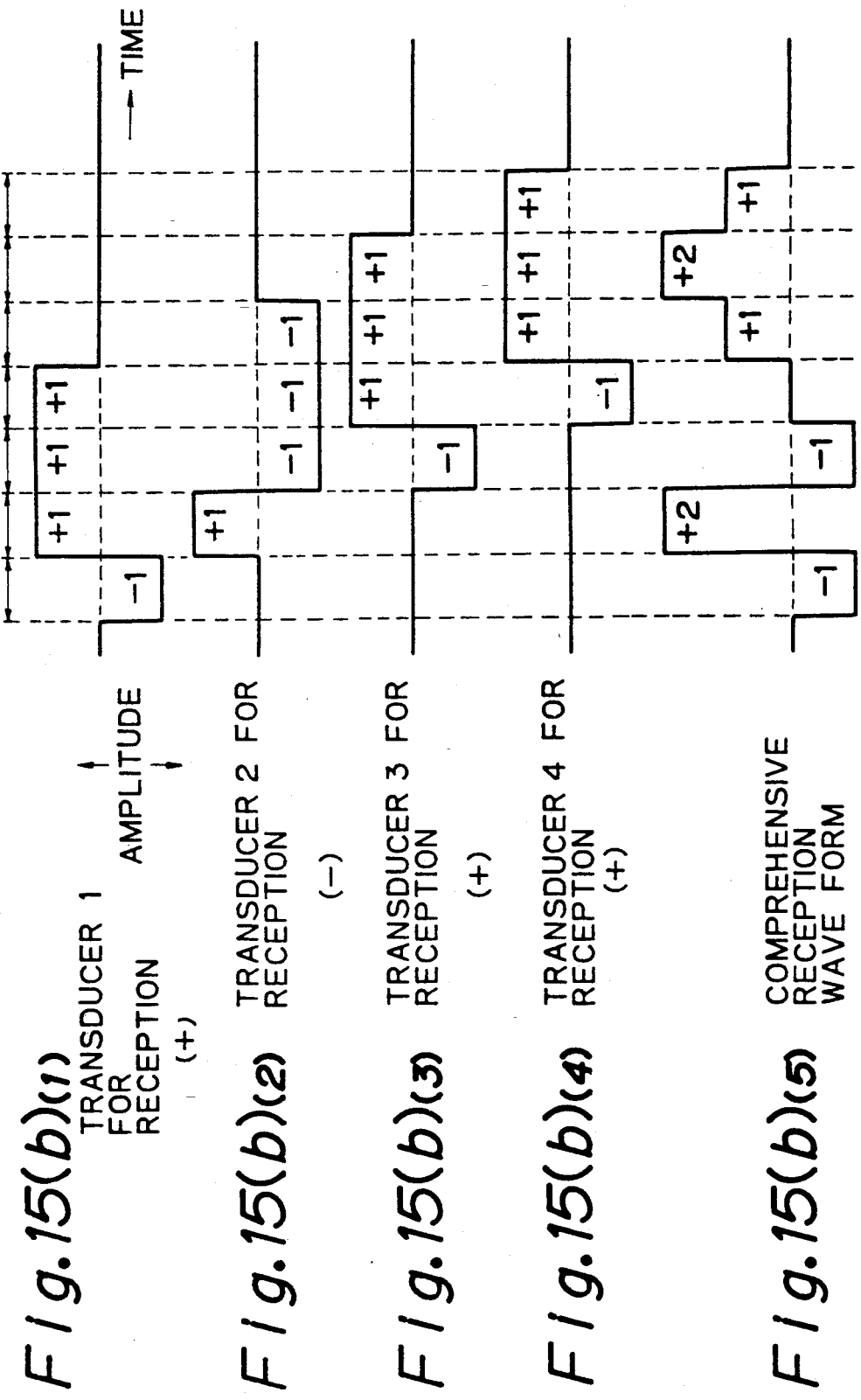

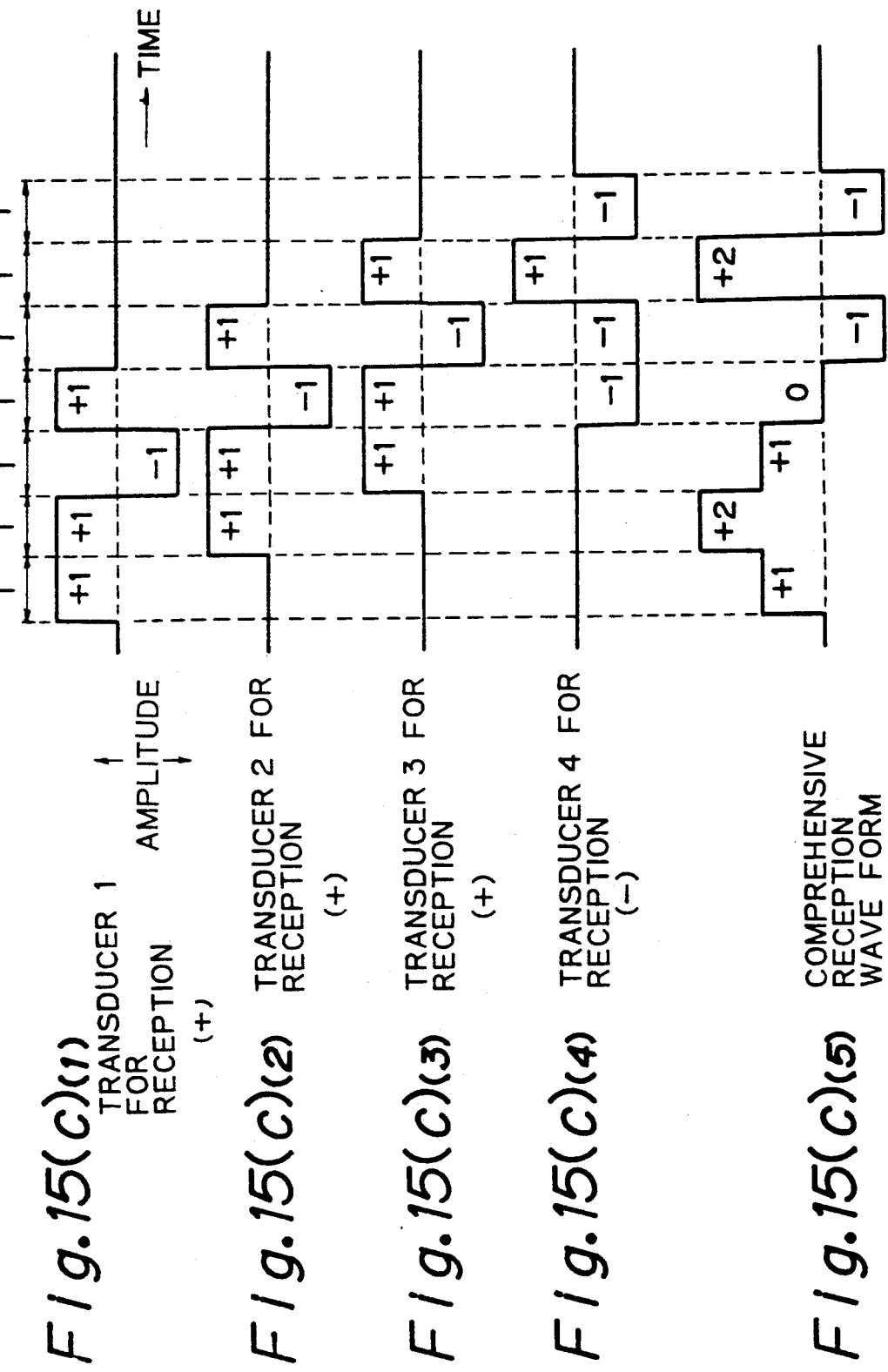

Fig.16 (a)
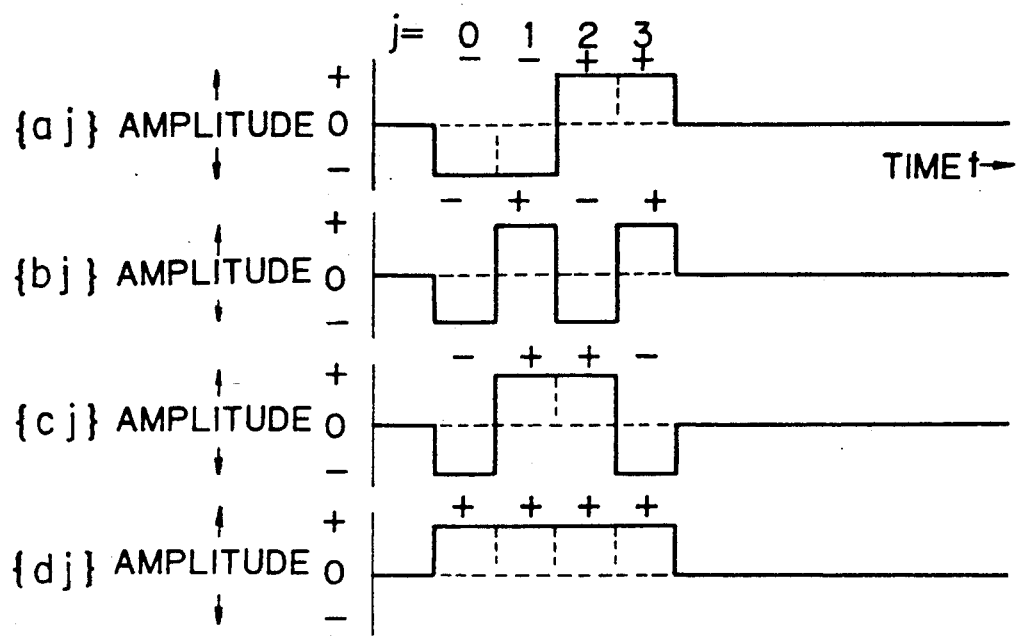
Fig.16 (b)
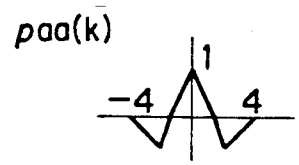
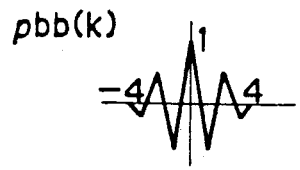
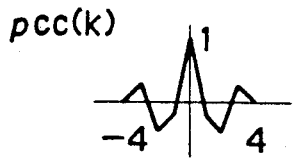
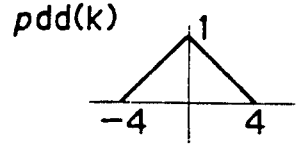
Fig.16 (c)
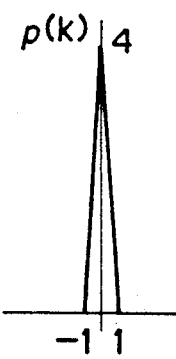

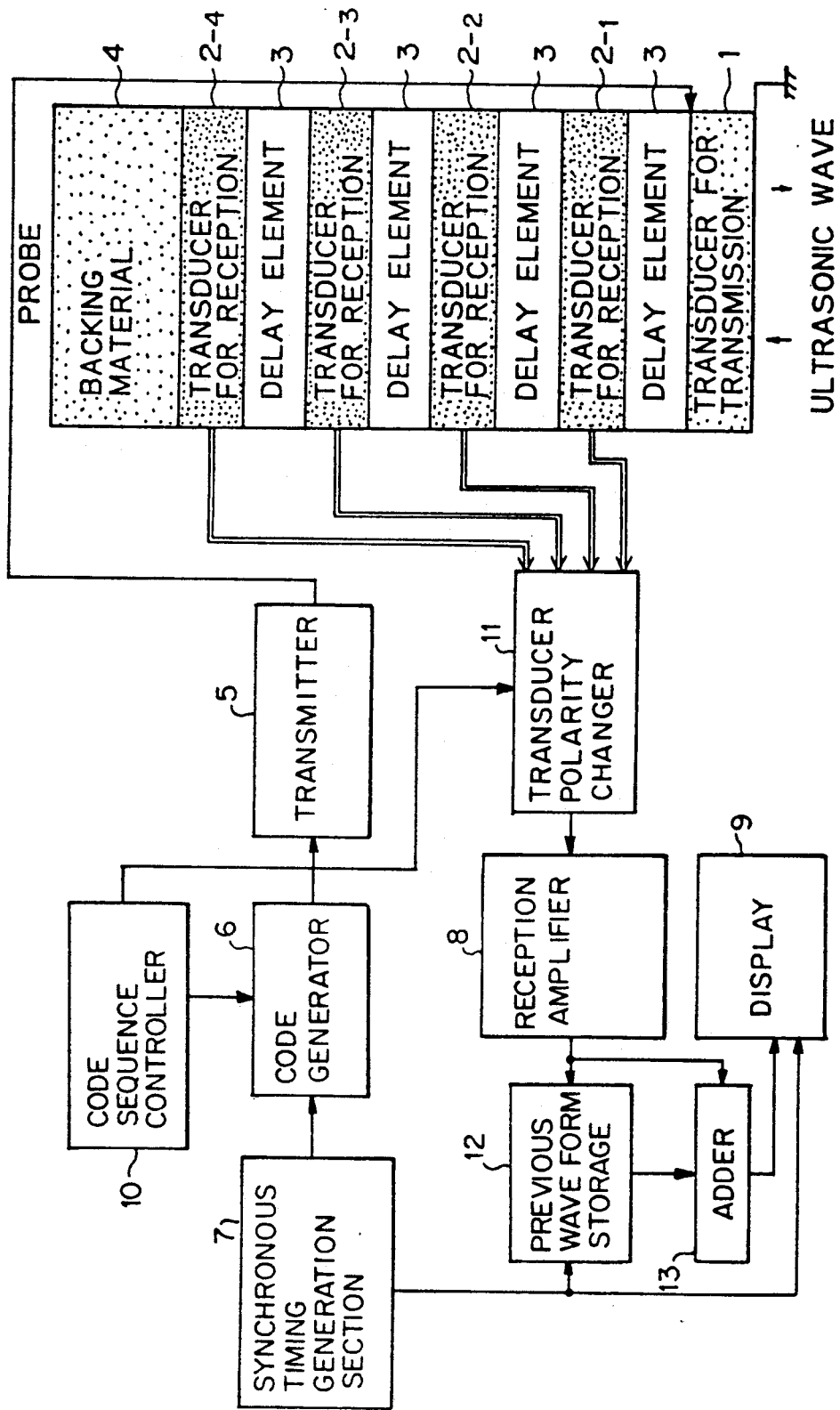

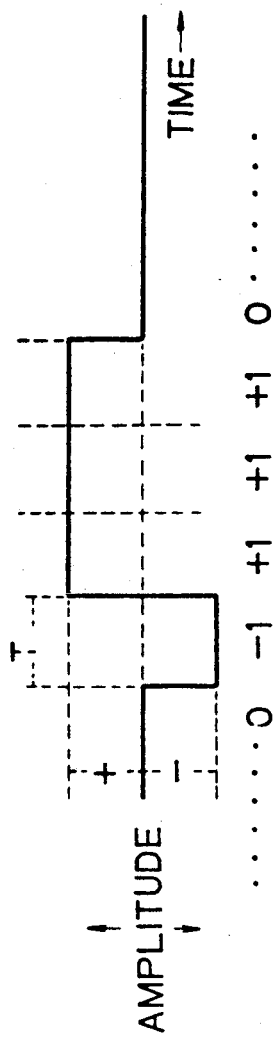
Fig. 18(a)(1) TRANSMISSION A
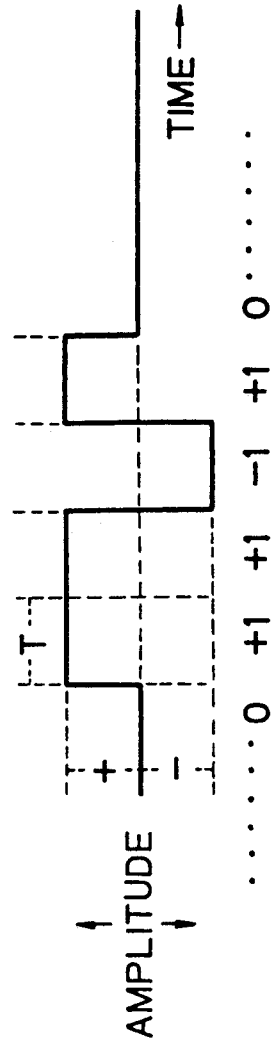
Fig. 18(a)(2) TRANSMISSION B

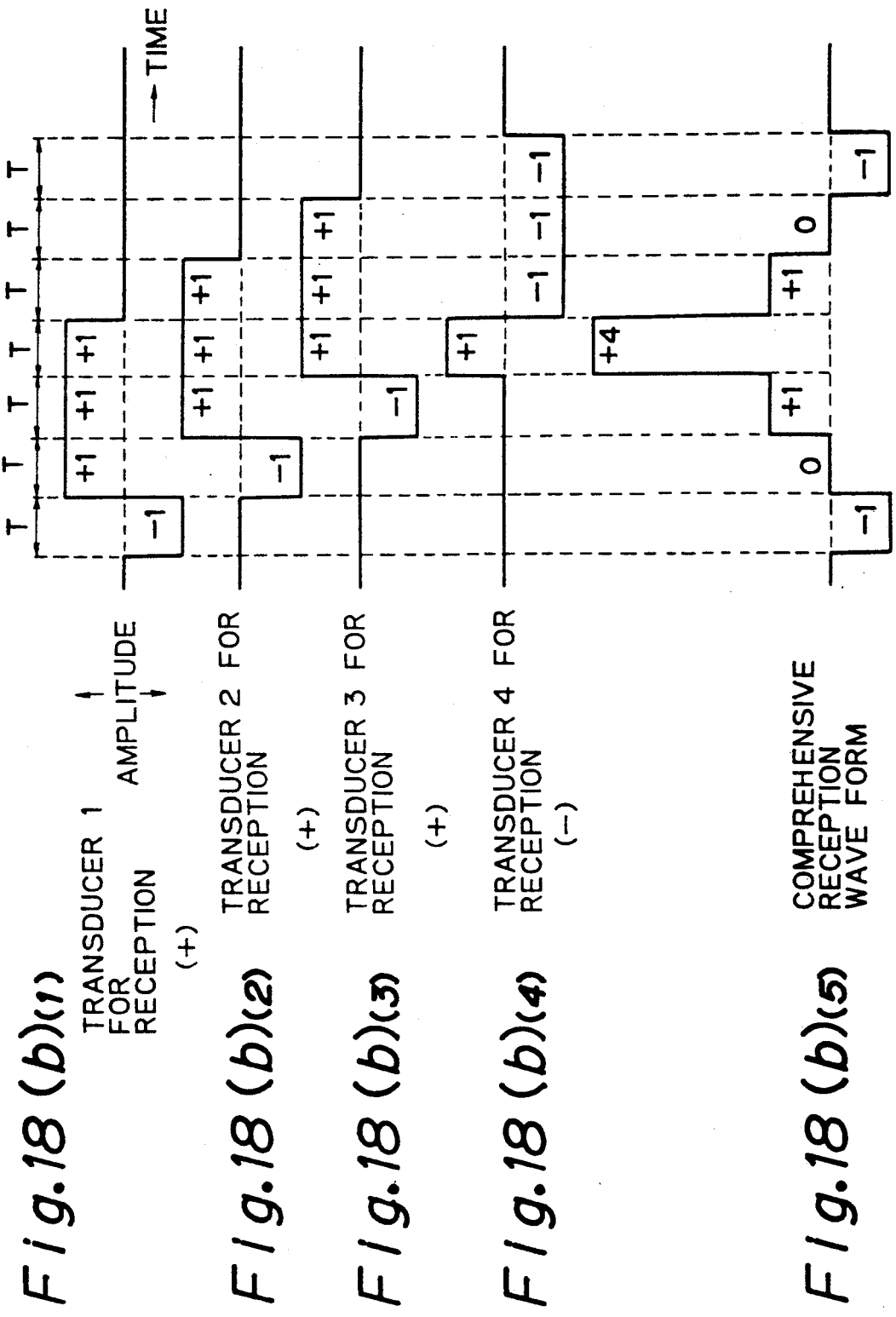

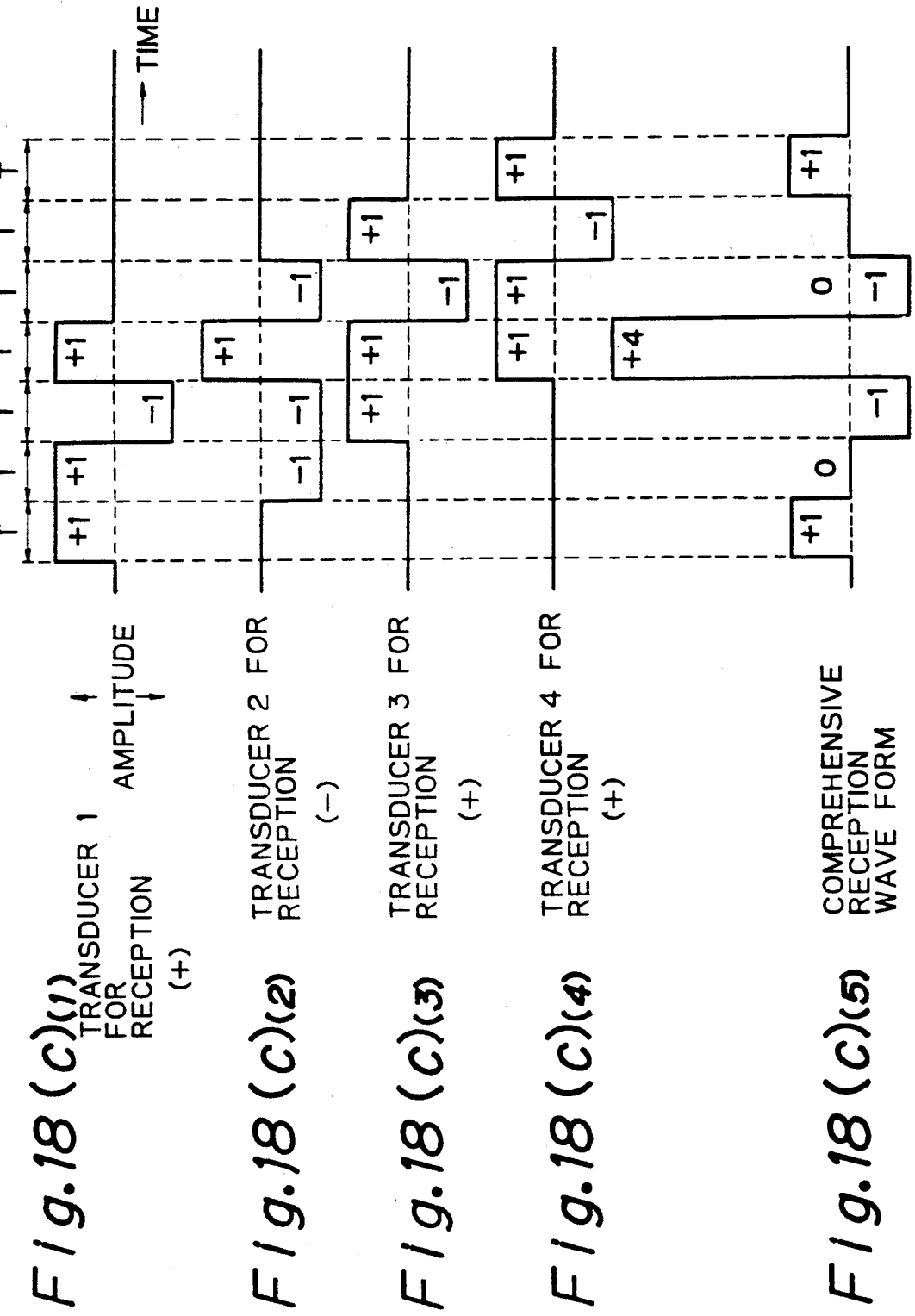

RECEPTION WAVE FORM OF SEQUENCES A+B

ULTRASONIC INSECTION APPARATUS

FIELD OF THE INVENTION

The present invention relates to an apparatus utilizing ultrasonic waves for detecting a flaw within a specimen and more particularly to an ultrasonic inspecting apparatus the signal-to-noise ratio (an S/N ratio) of which is improved.

DESCRIPTION OF THE PRIOR ART

As is well known, an ultrasonic inspecting apparatus for detecting a flaw in a metallic material has until recently been manually operated before the introduction of an automatic ultrasonic inspecting apparatus for the purpose of improving both the reliability and effectiveness of an inspection operation.

However, several problems have arisen in automatical inspection of flaws and one of them is devising a means to secure a good S/N ratio. While several factors make an S/N ratio worse, they may be roughly classified into two types, namely one being the case wherein a detecting signal level is low, and the other being the case wherein a level of a signal not used for detection (i.e. noise level) is high.

As to the case wherein the detecting signal level is low, it is considered in general that an input signal transmitted to a signal receiving amplifier is quite low.

The fact that, if the level of the detecting signal is low, it would be buried in amplifier noise produced by thermal ion motion in a receiving signal amplifier, thereby degrading the S/N ratio, has been publicly known as described on pages 177-181 of "Ultrasonic Testing Technology" published by Inc. Association-Nihon Nohritsu Kyokai, Feb. 25, 1980. In order to improve an S/N ratio in the case of a low input signal level, it is generally proposed to make an amplitude of an electric signal driving a probe larger so that the signal level is made higher. However, there is an upper limit with respect to an electric pulse voltage because of a limitation on the electric elements constituting a transmitting portion and a withstand voltage of a probe. Also, it is not permissible to make an electric voltage impressed on a signal transmitting portion higher for the purpose of prohibiting it from catching fire within an explosive atmosphere due to possible electric discharge.

As to the other case, there may be such problems as reverberation echo interfering with a high speed inspection.

As to interference of an echo due to reverberation which causes a problem in a high speed inspection, it becomes critical when the degree of attenuation of an ultrasonic signal within a specimen is low and a repetition frequency for inspection is high in an automatic inspection. Such a problem as above is encountered in a case where a subsequent transmission pulse is fed into a specimen during a time when the previous ultrasonic signal is under propagation within the specimen without being sufficiently attenuated.

This problem is understood as a phenomenon wherein the ultrasonic signal reflected at the time of previous transmission causes interference and it is generally coped with by lowering repetitive inspecting frequency which accompanies a lower inspection speed or by increasing the diffusion rate of an ultrasonic beam with the direction of the ultrasonic beam being slightly inclined.

Now, a conventional method hereinbefore practiced for improving an S/N ratio is explained hereunder.

It is generally considered to be effective in order to improve an S/N ratio in an inspection signal to utilize a correlation process. At first, the correlation process is described.

FIGS. 1(a) and (b) are graphs showing an operational principle of a Barker sequence as an example of a finite binary sequence having a sharp correlation function often used as a synchronizing pattern in a pulse transmission, FIGS. 2 are graphs explaining, similarly to FIGS. 1, an operational principle of a complementary sequence as an example of a finite binary sequence having a sharp correlation function, FIG. 3 shows a constitution of an ultrasonic inspecting apparatus performing a correlation process using a random code sequence, FIGS. 4(a)-(g) are drawings for explaining an operation of the apparatus shown in FIG. 3, and FIG. 5 is a graph indicating frequency characteristics of a transmitting signal, probe and specimen shown in FIGS. 3 and 4. FIG. 6 is a constitutional diagram of another prior art for realizing pulse compression. FIGS. 7(a) and (b) are explanatory diagrams for operation of the apparatus in FIG. 6.

FIGS. 1 show a Barker sequence as one of finite binary sequences having a sharp correlation function as disclosed in detail on, for example, pages 488–490 of "Coding Theory" published from Shokodo, June 30, 1981. In this case, the "binary" means two states of "+" and "−".

A correlation function $\rho_{aa}(k)$, wherein k is variable relative to a binarya sequence, is generally expressed by the following equation (1):

$$\rho_{aa}(k) = \frac{1}{n} \sum_{j=0}^{n-1} a_{j+k} \cdot a_j \tag{1}$$

where n is the length of the sequence.

In this case, a finite sequence "a" is treated as an infinite length sequence having series of "0" at the both sides as expressed by the following equation (2):

$$\{a_j\} = 0 \ldots 0 a_0 a_1 \ldots a_{n-1} 0 0 \ldots 0 \tag{2}$$

Since $a_j = 0$ for the range of $j \leq -1$ and $j \leq n$, the equation (1) may be converted to the following equation (3):

$$\rho_{aa}(k) = \begin{cases} \frac{1}{n} \sum_{j=0}^{n-1-|k|} a_{j+|k|} \cdot a_j; & |k| < n \\ 0; & |k| \geq n \end{cases} \tag{3}$$

As seen from the equation (3), noise levels such as thermal noise having no correlation with the sequence may be reduced, and a correlation process is considered to be an effective means for improving an S/N ratio relative to thermal noise. This is also considered to be effective against random noise interfering with an inspecting apparatus such as electric noise derived from a motor or welding equipment.

Further, at the time of inspecting flaws, a certain sequence whose autocorrelation function $\rho_{aa}(k)$ has a sharp peak at $k=0$ and becomes sufficiently small in another range $(0 < |k| < n)$ is required.

An absolute maximum value $|\rho|_{max}$ in a range other than the peak (i.e. referred to as a range sidelobes) for evaluating an autocorrelation degree of a binary sequence is expressed by the equation (4) as below:

$$|\rho|_{max} = max\{|\rho_{aa}(k)|\} \quad (4)$$

$$0 < k < n$$

In this connection, a finite binary sequence satisfying $$|\rho|_{max} = 1/n$$

is specifically referred to as a Barker sequence for distinction.

FIG. 1(a) shows a signal of binary sequence expressed by the following equation (5) wherein n=7:

$$\{a_j\} = + + + - - + - \quad (5)$$

FIG. 1(b) shows an autocorrelation function calculated based on the equation (3) wherein $-n \leq k < n$. It is noted that the maximum value is recorded at k=0 and, at the other portions, 1/n is the maximum (in this instance 1/7).

FIGS. 2 show a complementary sequence which is a finite binary sequence having a sharp correlation function as disclosed in detail on, for example, pages 488-490 of "Coding Theory" published from Shokodo, June 30, 1981.

From the equation (3), it is clear that there is no finite binary sequence whose autocorrelation function becomes zero at all points other than at the point k=0.

However, there may be a case wherein the sum of the respective autocorrelation functions $\rho_{aa}$ (k) and $\rho_{bb}$ (k) of two binary finite sequences $\{a_j\}$ and $\{b_j\}$ each having a length of n, i.e.

$$\rho(k) = \rho_{aa}(k) + \rho_{bb}(k) \quad (6)$$

becomes zero at all points other than at the point k=0.

These two sequences $\{a_j\}$ and $\{b_j\}$ are referred to as a complementary sequence.

FIG. 2(a) shows an example of a complementary sequence wherein n=4 and represents binary sequences expressed by the equation (7):

$$\{a_j\} = + + + - \{b_j\} = + - + + \quad (7)$$

FIG. 2(b) shows autocorrelation functions of $\{a_j\}$ and $\{b_j\}$ in the range $-n \leq k < n$ and calculated based on the equation (3).

FIG. 2(c) indicates the sum $\rho(k)$ of the respective autocorrelation functions calculated based on the equation (6). As seen from this drawing, it is theoretically possible to make levels of range sidelobes zero.

FIG. 3 shows an example discussed in detail on pages 888-891 of "High-Speed Digital Golay Code Flaw Detection System, IEEE 1981 Ultrasonic Symposium Proceeding", by B. B. Lee and E. S. Furgason (hereinafter referred to as Reference A) wherein 15 designates a probe, 5 a transmitter, 6 a code generator, 14 an analog correlator, 9 a display, 21 a bipolar converter, 18 a selector, 19 a digital delay line, 20 a system controller, 16 a water bath and 17 a target.

FIGS. 4 are drawings for explaining the operation of FIG. 3. FIGS. 4(a), 4(b), 4(c) and 4(d) indicate a synchronizing signal, a code sequence, a selection signal and an output of the bipolar converter 21, respectively.

With the synchronizing signal of FIG. 4(a) from the system controller 20, the code generator 6 generates a binary code sequence such as shown in FIG. 4(b). The code sequence generated at the code generator 6 is inputted into the bipolar converter 21 connected to the transmitter 5 through the selector 18 as well as into the digital delay line 19. The code sequence inputted into the bipolar converter 21 connected to the transmitter 5 is given an amplitude of +/− depending on its code at the bipolar converter and, thence, the output of FIG. 4(d) is inputted into the transmitter 5 and applied, as a transmission pulse with being amplified, to the probe 15. An ultrasonic signal radiated from the probe 15 is reflected at the target 17 within the water bath 16, fed back as a receiving signal to the probe 15 and, thence, directed to the analog correlator 14.

The code sequence of FIG. 4(b) inputted into the digital delay line 19 is delayed by a time (t') designated by the system controller 20, inputted into the other bipolar converter 21 as a reference code sequence [FIG. 4(f)] and directed, as a reference signal for a correlation processing with an amplitude of +/− being given at the bipolar converter 21 depending on the input code, to the analog correlator 14.

Within the analog correlator 14, the right side operation of the equation (3) is performed with using a multiplier 14a and an integrator 14b wherein the delay time "t'" of the reference signal code [FIG. 4(f)] corresponds to "k" in the equation (3). Therefore, an inspected wave form after the correlation process can be displayed in the display 9 by varying the delay time t' at each cycle of repetitive transmission in the system controller 20.

With employment of the correlation process as above, an S/N ratio has been improved.

In a case where the process of the complementary sequence explained regarding FIG. 2 is carried out using the above apparatus, some memory means and some means for summing the operational results of the correlation operation on two sequences would be required.

FIG. 6 illustrates an example in which the probe as described in detail, for example, in the literature entitled "Non-destructive Inspection" Vol. 32, No. 2, p. 146-147 is endowed with the function of pulse compression. In FIG. 6, numeral 1 designates transducers for transmission, numeral 3 delay elements serving also as insulation between the transducers, numeral 4 backing materials adapted to absorb the ultrasonic wave irradiated onto the back surface of the transducers, and numeral 2 transducers for reception.

FIG. 7 is the diagram explaining the operation of the example shown in FIG. 6. FIG. 7(a) shows the wave forms for transmission while FIG. 7(b) shows the wave forms for reception.

When the transducers for transmission $1_1$-$1_4$ are driven in the identical timing so as to generate transmission pulses, the ultrasonic wave signals which have been generated by the transducer $1_1$ for transmission emerge at the location designated by (1) in FIG. 7(a). Furthermore, the ultrasonic wave signals which have been generated by the transducer $1_2$ for transmission will emerge at the location designated by (2) in FIG. 7(a) after the lapse of the time T through the delay element 3 and the transducer $1_1$ for transmission. Similarly, the ultrasonic wave signals which have been generated by the transducer $1_3$ emerge at the location designated by (3) in FIG. 7(a) and the ultrasonic wave signals which have been generated by the transducer $1_4$ emerge at the location designated by (4) in FIG. 7(a). Those ultrasonic waves which have been made comprehensive are the comprehensive wave form for transmission shown by (5) in FIG. 7(a). It is to be noted that this wave form will eventually be identical to the transmission signal in a Barker sequence in the case of N=4. It is also to be noted that the ultrasonic wave which has been irradiated onto the back surface of a transducer will be absorbed and attenuated by the backing material 4 and will not be returned as an ultrasonic wave. Next, the echo reflected by the reflection source such as the flaw in the test piece will be returned to the reception probe 10 by maintaining a substantial wave form as designated by (5) in FIG. 7(a). The transducers $2_{-1}$-$2_{-4}$ for reception are so connected as shown in FIG. 6 that only the polarity of the transducer $2_{-3}$ for reception is reversed.

This constitution merely constitutes the reversed version of the constitution of the transducer for transmission and is connected such that the time order is reversed in relation to the Barker sequence of N=4 as used for transmission as above-described.

The wave forms of the electric signals which have received by the transducers for reception corresponding to the transducers for reception $2_{-1}$-$2_{-4}$ are designated respectively as (1), (2), (3), (4) in FIG. 7(b). The wave form (5) in FIG. 7(b) designates the wave form as the result of summing the wave forms (1), (2), (3), (4) and allows the pulse compression to be made of the Baker sequence without any special hardware for correlation processing.

It is here to be understood that for execution of correlation processing in the example shown in FIG. 3 by the ultrasonic flaw detector as explained above according to a prior art which executes the correlation processing by using a binary finite length sequence, a special hardware for a correlator is required and for this reason, a tremendous number of multiplication and addition operations are required for the correlation operation. Since the wave forms after the pulse compression is obtained after the calculation, it is impossible to obtain the wave forms at a real time.

According to the example shown in FIG. 6, a plurality of transducers are sandwiched and positive and negative encodement is realized by the polarized directions. As a consequence, encodement of the wave forms for transmission can be executed easily. Furthermore, the probes for reception are similarly constituted as the correlator so that pulse compressed wave forms may be obtained. However, according to this example, transmission signals must be delivered to a plurality of transducers simultaneously at the time of transmission. As a result, the transmission energy will be dispersed by one fourth for each transducer for transmission and the level of the transmission energy from the respective transducers for transmission will be reduced, so that only the transmission energy equivalent to the one available without pulse compression will be delivered, or the effect of pulse compression cannot be attained.

Incidentally, in a conventional ultrasonic inspecting apparatus shown in FIG. 3, transmission signals are given at a level of +/− to a probe. FIG. 5 shows frequency characteristics of a probe, etc. used for a flaw inspecting apparatus and "a" of FIG. 5 indicates a frequency response of a probe 15, "b" a frequency characteristic of a transmission signal wave form used in a conventional apparatus and "c" a frequency response characteristic of a specimen in which, for example, attenuation is relatively large. There has been a problem in that the transmission signal applied to the probe 15 possesses, due to its feature of a rectangular pulse signal, its energy in a relatively low frequency range and the energy in the low frequency range has not been effectively utilized by the probe 15 due to its frequency characteristics.

In addition to the above, it is seen that a frequency characteristic of an ultrasonic beam radiated into a body of a specimen depends on a frequency characteristics of a probe because the frequency range of a transmission signal is wide. This matter indicates that manufacturing tolerances of a probe affect flaw detection frequency whereby there has been a problem in that results of flaw detection would not be constant if the probe is switched to the other. Further, FIG. 5 indicates that a certain part of a frequency range wherein a probe is effectively used is cut off depending on an attenuation characteristic of a specimen. Therefore, there has been another problem in that noise may remain at a certain level in a case where attenuation in a specimen is high and an S/N ratio is likely to become worse even if an S/N ratio is improved by a conventional correlation process whereby enlarging of an amplitude in a transmission signal must be carried out.

Also, there has been a further problem in that some components of a code sequence may remain and so cannot be reduced in the case where there are an interfering echo due to an internal construction of a specimen and a reverberation echo in a high speed inspection.

SUMMARY OF THE INVENTION

The present invention has been provided to solve the problems as above-described and has it as an object to improve an S/N ratio in a real time without using various special correlators for computation of correlation. Furthermore, another object of the present invention is to provide, in addition to said object, an ultrasonic inspecting apparatus which is capable of reducing external noises and also reducing the range side lobe.

The ultrasonic inspecting apparatus according to the present invention is adapted to transmit from a single transducer for transmission those transmission signals corresponding to binary code sequences of length N with a sharp autocorrelation and to place each of N number of transducers for reception over the other in the configuration having the reversed time order of the binary code sequences.

Furthermore, the ultrasonic inspecting apparatus according to an another invention of the present invention is adapted to generate the wave forms having the frequency component $f_0$ for each of the positive or negative codes in the binary code sequence having a sharp autocorrelation and change the phases corresponding to the positive/negative codes by 180°.

According to the present invention, it is possible to increase the entire transmission energy by using the single transducer for transmmission to distribute the transmission energy over the time axis. It is also possible to execute the autocorrelation processing in a real time by use of the placed transducers for reception.

Further, according to another embodiment of the present invention, it is possible to allocate almost all of the energy of transmission signals to the frequency range through which the ultrasonic transducer passes, by assigning the wave forms having the frequency component $f_0$ to the codes, so that utilization efficiency of the transmission energy may be improved.

BRIEF DESCRIPTION OF THE DRAWINGS

FIGS. 2(a), (b) and (c) are explanatory diagrams of a complementary sequence for explaining a prior art;

FIGS. 7(a) and (b) are explanatory diagrams for operation of the apparatus in FIG. 6;

FIG. 14 is a constitutional diagram of the ultrasonic inspecting apparatus showing the second embodiment of the present invention;

FIGS. 15(a), (b) and (c) are explanatory diagrams of the apparatus in FIG. 14;

FIGS. 16(a), (b) and (c) are explanatory diagrams with regard to the effect of the third embodiment of the present invention;

FIG. 17 is a constitutional diagram of the ultrasonic inspecting apparatus illustrating the third embodiment of the present invention;

DETAILED DESCRIPTION OF THE PREFERRED EMBODIMENTS

Figure 8:
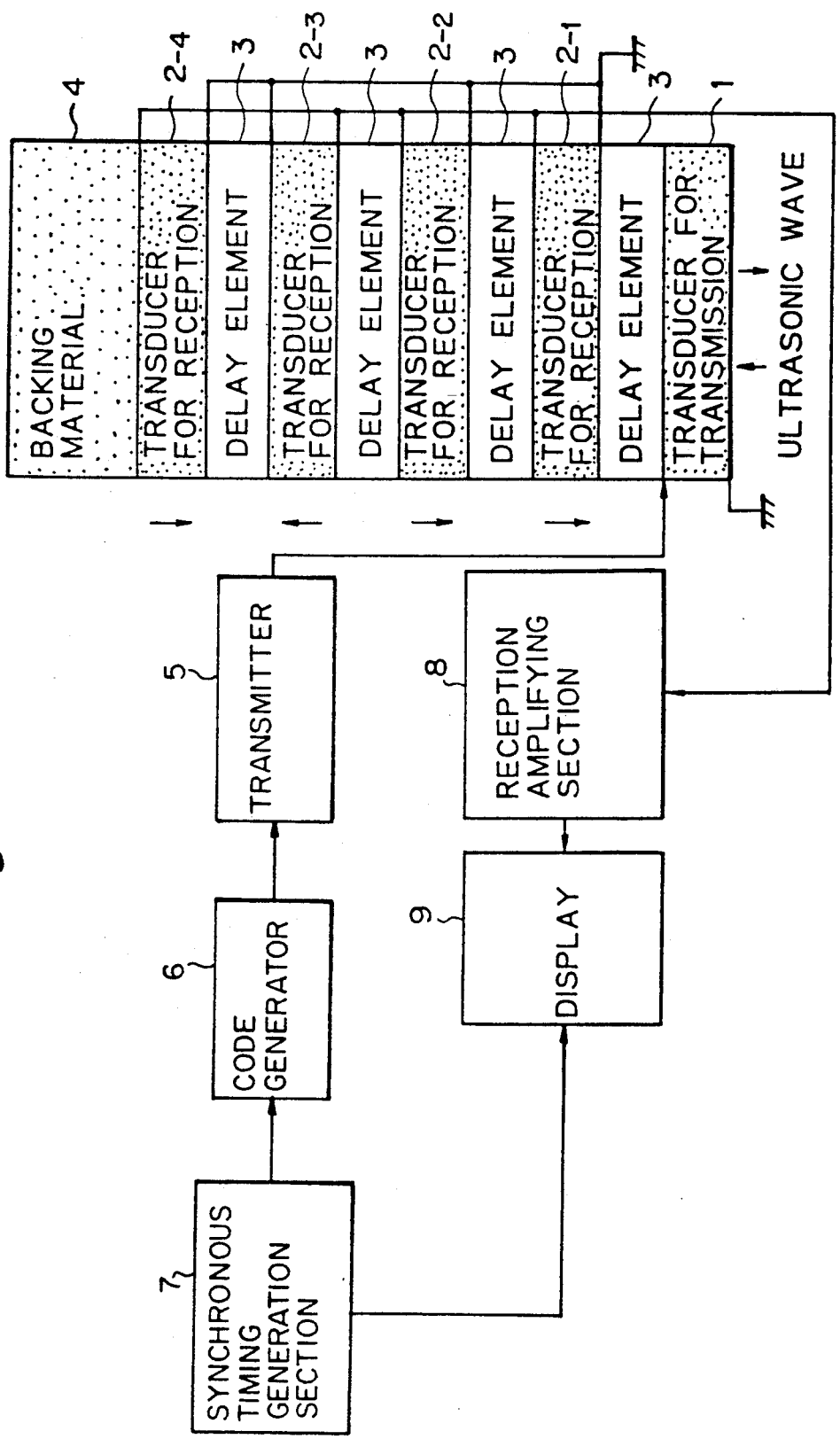
FIG. 8 is a constitutional diagram of the ultrasonic inspecting apparatus illustrating the first embodiment of the present invention.

FIG. 8 is an explanatory diagram of the ultrasonic inspecting apparatus showing the first embodiment of the present embodiment and numerals 1, 2, 3, 4, 5, 9 are identical to those in the apparatus according to a prior art as above explained. Numeral 7 designates a synchronous timing generation section adapted to control the transmission timing. Numeral 6 designates a code generator connected to the synchronous timing generation section and adapted to generate a positive and negative binary finite code sequence having a sharp autocorrelation function every time T, and numeral 8 designates a reception amplifying section adapted to amplify the ultrasonic signals which have been received by the reception transducer 2.

Figure 9:
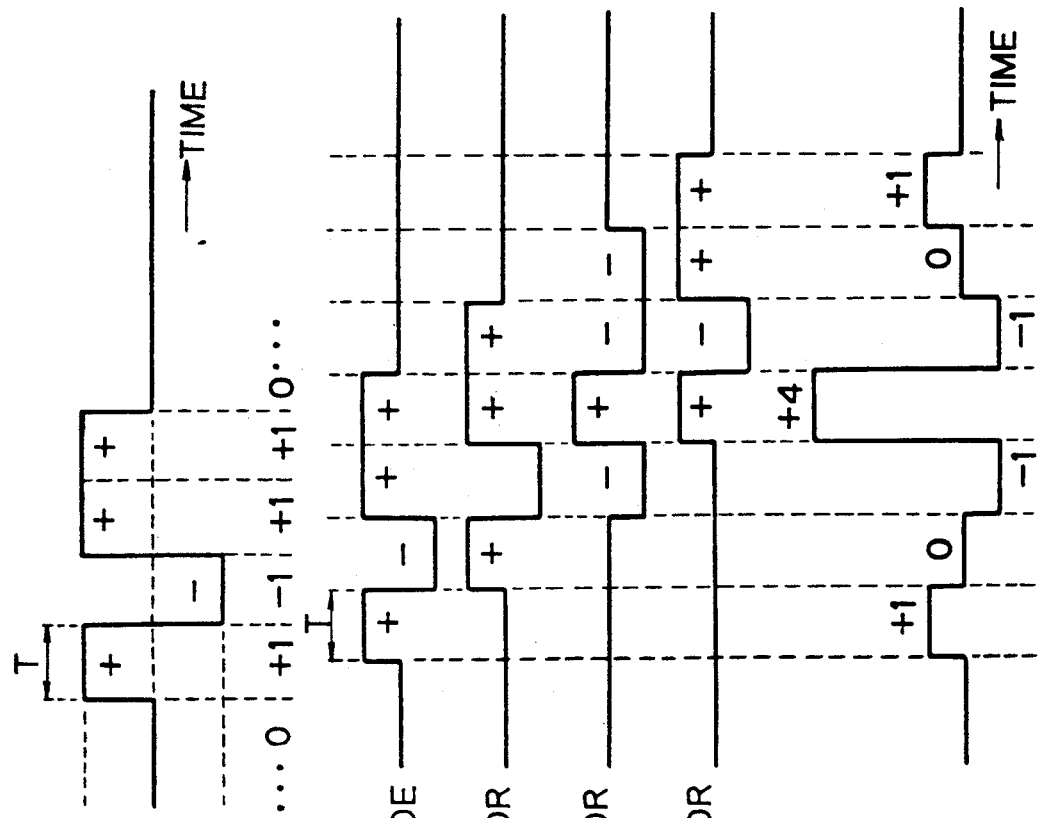
FIGS. 9(a) and (b) are explanatory diagrams for operation and effect of the apparatus shown in FIG. 8.

FIG. 9 is an explanatory diagram which explains the operation of the apparatus, FIG. 9(a) illustrates a code sequence having a sharp autocorrelation function (in this example, a Barker sequence) which is to be output from the code generator 6 by the synchronous signals generated by the synchronous timing generation section 7, and FIG. 9(b) designates the inspecting wave forms received from each of the transducers of the inspecting probe for reception and the comprehensive reception wave forms to be input to the reception amplifying section 8.

According to the ultrasonic inspecting apparatus constituted as above, the synchronous signals are input to the code generator 6 by the synchronous timing generation section 7. At the code generator 6, positive and negative codes of binary finite code sequences having predetermined sharp autocorrelation function are held for each code during the time T equivalent to the ultrasonic propagation time between adjacent transducers of the transducers 2 for reception and then output. The wave form at this time is shown in FIG. 9(a). A presettable shift register may be used as the means of generating codes wherein a code sequence is input in the shift register and a shift clock for a unit time T is used to easily generate codes. The code sequences which have been generated by the code generator 6 with the time interval T for each code are amplified at the transmission section and applied to the transducer 1 for transmission.

The transmission signals thus applied to the transmission transducer 1 are converted to ultrasonic signals and input to the test piece, and the signals reflected by such reflectors as flaws are returned to the transducers 2-1-2-4 for reception.

According to the present embodiment, the transducer 2 for reception are consisted of four of transducers and each of them is placed over the other with the delay element interposed therebetween, each of interposition being equidistant, and the ultrasonic propagation time between the transducers is T. It is to be noted that in the present embodiment the applied electric fields to the transducers for reception are assigned to the positive or negative component in the code sequence. In other words, if the negative component in the code sequence is desired to be changed to the positive component, or, vice versa, the grounding side of the electrode of the transducer is so inverted that the phase of the reception signals will be reversed. Furthermore, the series of the polarities of the outputs of the respective transducers for reception is caused to correspond to a code sequence in such a way that the time order is inverted relative to the code order of the code sequence which has been used for transmission.

It is to be noted in the present embodiment that the direction of polarization of the respective transducers for reception is made identical in advance and the grounding side (or the direction of the electric field applied to the transducers) of the transducer electrodes of the respective transducers is selectively inverted so that the polarities of the output of the respective transducers for reception may be caused to correspond to the positive or negative component in a code sequence. In addition, even if the grounding side of the electrode of the respective transducers is all caused to be identical, and the direction of polarization of any of the transducers for reception is selectively inverted, the same result may be obtained.

According to the present embodiment, since the code sequence to be transmitted is arranged with the sequence of [+ − + +] and the time order of the sequence is inverted at the time of reception, the code may be received in the order of [+ + − +]. As a consequence, the transducers for reception are so arranged that the transducer for reception 2-1 has [+], the transducer 2-2

[+], the transducer 2-3 [−] and the transducer 2-4 [+], respectively. An example of the ultrasonic signal which has been converted to an electric signal by the transducer for reception 2-1 is illustrated in FIG. 9(b) (1). Only the polarity is shown. The following is the same. Since the ultrasonic signal which has been converted to an electric signal by the transducer for reception 2-2 is fed via the delay element 3 and the transducer for reception 2-1, it is as shown in FIG. 9(b) (2) with the delay of the time T due to passage through the delay element 3 and 2-1. Since the ultrasonic signal which has been converted to an electric signal by the transducer for reception 2-3 is further delayed by the time T in the same manner as the signal received by the transducer for reception 2-2 and corresponds at the same time to the [−] code of the previous code sequence, it will have the inverted phase relative to those of the transducers 2-1 and 2-2 for reception as shown in FIG. 9(b) (3). With regard to the transducer for reception 2-4, since it corresponds to the code of [+], the same wave form as those of the transducers 2-1 and 2-2 for reception is obtained with the further delay of time T as compared to the transducer for reception 2-3 as shown in FIG. 9(b) (4). Since the signals received by the respective transducers 2 for reception are coupled in parallel, they are input to the reception amplifying section 8 as the comprehensive reception wave form as shown in FIG. 9(b) (5) and displayed at the display 9 in a real time.

As a result, the signals thus received are improved in an S/N ratio by four times.

Figure 6:
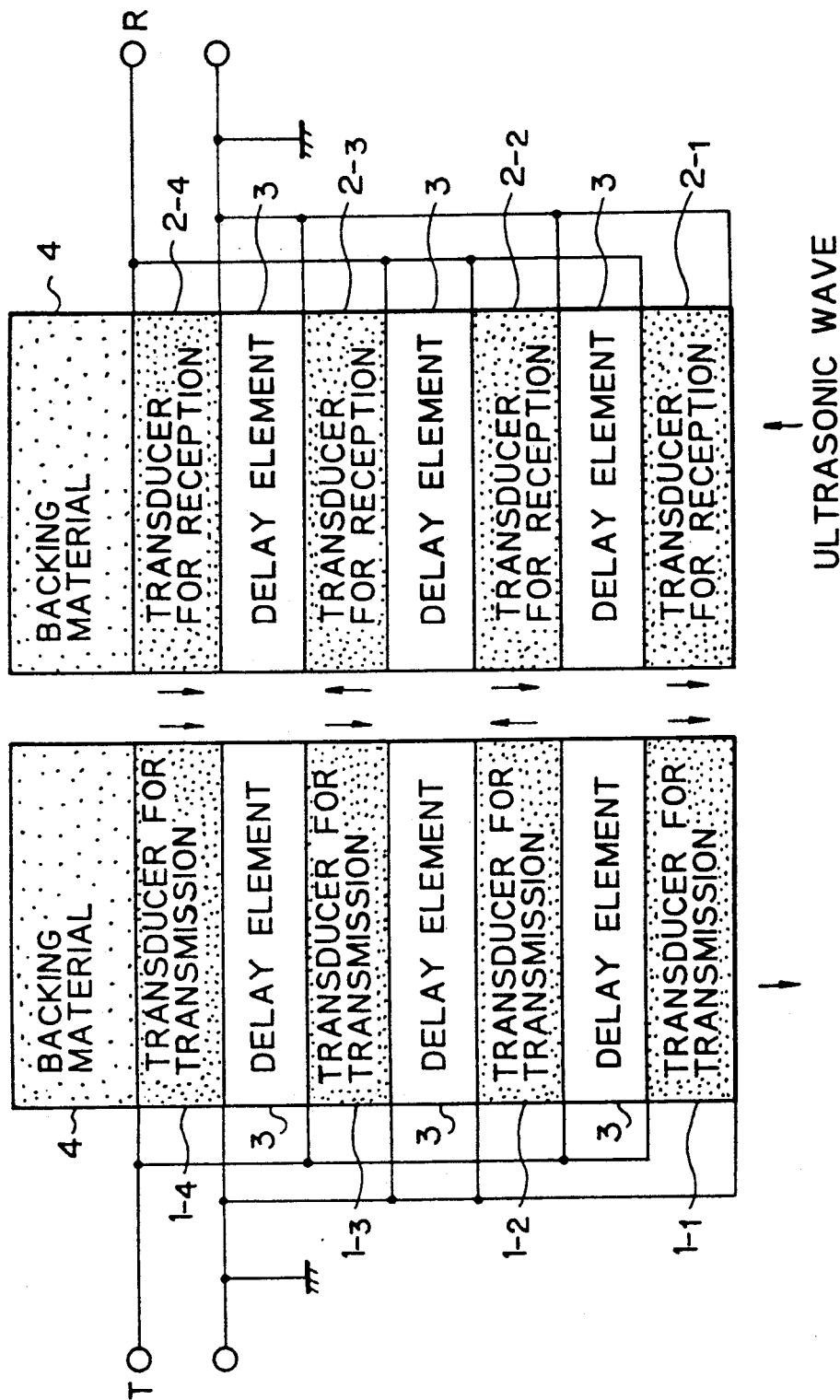
FIG. 6 is a constitutional diagram of another prior art for realizing pulse compression.

In the first embodiment of the present invention the complicated correlation processing hardware may become unnecessary and the pulse compression is available in a real time. Furthermore, since a single transducer for transmission is employed to disperse the transmission energy on the time axis, four times as much as of the transmission energy may be supplied to the probes compared to the conventional method of placing on the other of the transducers as shown in the left side of FIG. 6 to transmit a transmission signal corresponding to a code sequence whereby S/N ratio may be further enhanced.

It is to be noted that although the time T corresponding to the code intervals has been used as the constant to be defined by the probes in the above-described embodiment, if a time adjustment function is added to the code generator 6 in consideration of the possibility of use of the probes with different intervals between the transducers or use of the probes with different frequencies, the effect of pulse compression provided by the present invention may also be realized in the various probes having similar construction.

Figure 5:
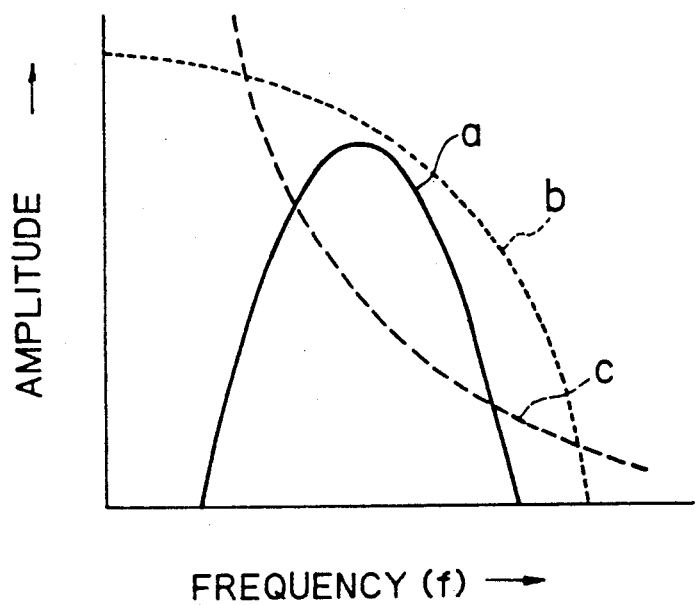
FIG. 5 is an explanatory diagram for explaining the problems according to the prior art.

It can be seen from the foregoing description that S/N could be largely enhanced due to the pulse compression effect as the consequence of the present invention. However, it is also clear from the example in FIG. 5 that although the transmission signals keep energy even in a relatively low frequency range due to the signals being pulse signals, such energy in the low frequency range cannot be effectively used according to the frequency characteristics of the transducers 1 for transmission and the transducers 2 for reception. In view of this fact, if the encoding phase modulation section is added to the code generator as shown in FIG. 10, S/N ratio may be still further enhanced.

Figure 10:
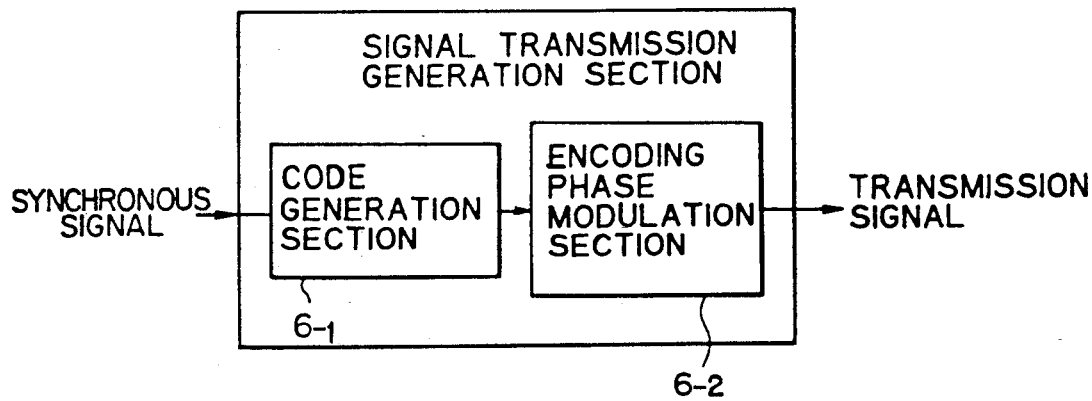
FIG. 10 is a constitutional diagram of a variant of a code generator shown in FIG. 8.

FIG. 10 illustrates a constitution of the improved code generator and the code transmission section. In FIG. 10, numeral 6-1 designates the code generation section adapted to generate similar code sequences as generated by the code generator 6. Numeral 6-2 designates the encoding phase modulation section adapted to receive the binary code sequences having positive and negative components input from the code generation section 6-1 and generate wave forms having the frequency component of $f_o$ and changed by 180° depending on the positive or negative codes.

Figure 11A:
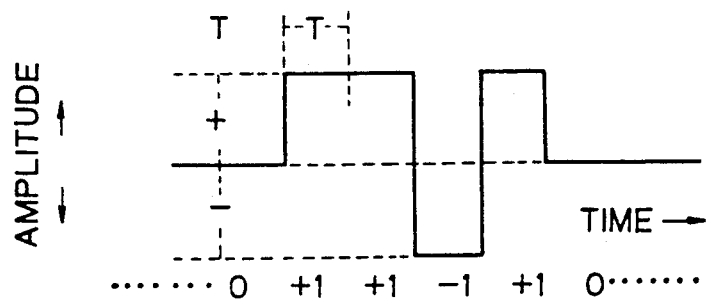
FIGS. 11(a) and (b) and FIG. 12 are explanatory diagrams with regard to the operation and effect of the apparatus shown in FIG. 10.
Figure 11B:
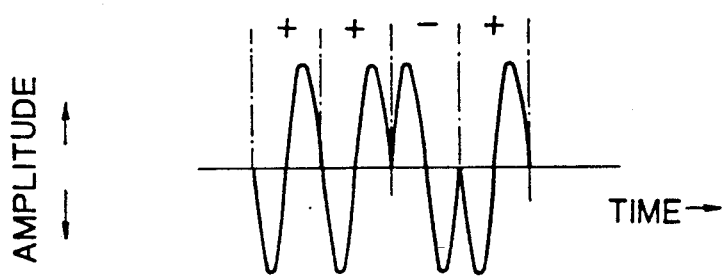

FIGS. 11(a) and (b) are explanatory diagrams for the operation of the system shown in FIG. 10. FIG. 11(a) illustrates a code sequence having the sharp autocorrelation function (a Barker sequence in this example) output from the code generation section 6-1 and FIG. 11(b) illustrates a transmission signal generated by the encoding phase modulation section 6-2.

Figure 12:
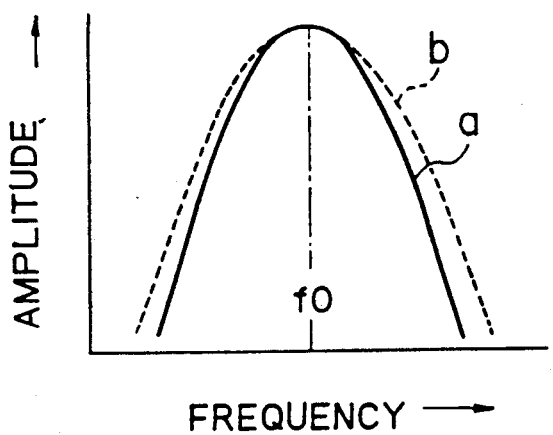

FIG. 12 illustrates a frequency response characteristics of an ultrasonic probe and the frequency characteristics of the transmission signals generated by the encoding phase modulation section. In FIG. 12, "a" designates the frequency response characteristics of the ultrasonic probe and "b" designates the frequency characteristics of the transmission signals.

The code sequence as shown in FIG. 11(a) which has been generated by the code generation section 6-1 is input to the encoding phase modulation section 6-2. The encoding phase modulation section 6-2 is adapted to generate the wave forms having a frequency component of $f_o$ at the phase of "zero" degree in the case of the positive code and at the phase of 180° in the case of the negative code respectively in the period of time T. An example of the wave forms generated as above is illustrated in FIG. 11(b). It is to be noted in this instance that the wave forms allocated for each code have a sine wave form of one cycle in the case of the code being positive and a sine wave form with the phase changed by 180° in the case of the code being negative. An example of the means for generating such wave forms is the one which stores in advance the wave form data in a memory in respect of positive and negative codes, reads out such data for each code and generates the wave forms as shown in FIG. 11(b) by using for example a digital-analogue converter. As the result, the relation as shown in FIG. 12 may be attained if the transmission signals having the frequency component $f_o$ are applied to the probes and the frequency $f_o$ is adjusted to the central frequency of the transducers 1 for transmission and the transducers 2 for reception. Different from the conventional transmission signals, the transmission signals have almost no energy present in the low frequency range. As the consequence, a majority of the transmission energy will be allowed to pass through the transducers for transmission. Compared to the case of using the code generator which does not use the encoding phase modulation section, the transmission signals having the code sequence and a higher energy utilization efficiency may be applied to the probes, so that the S/N ratio may further be enhanced.

Figure 1A:
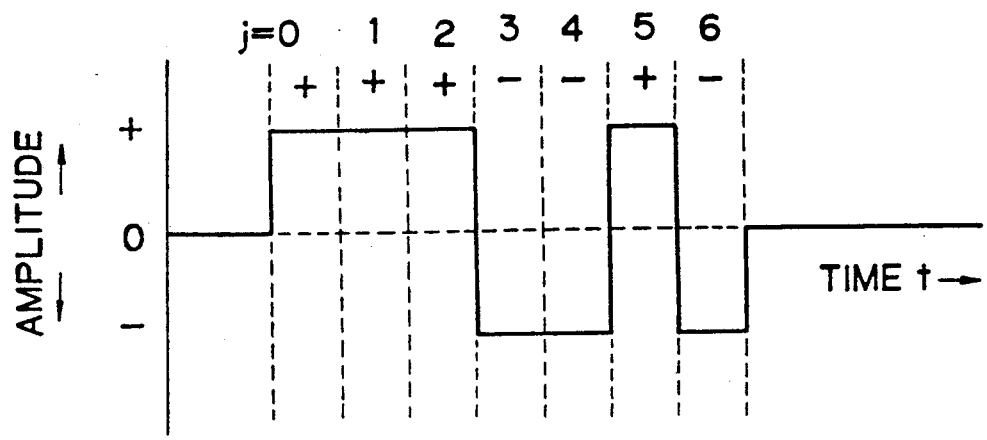
FIGS. 1(a) and (b) are explanatory diagrams of the Baker sequence for explaining a prior art.
Figure 1B:
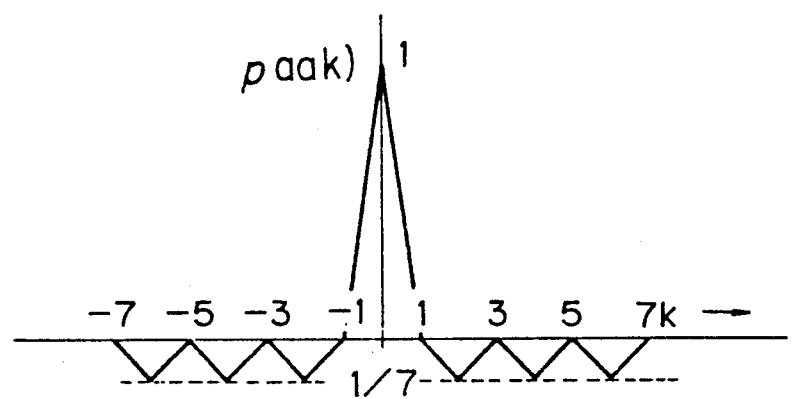
Figure 3:
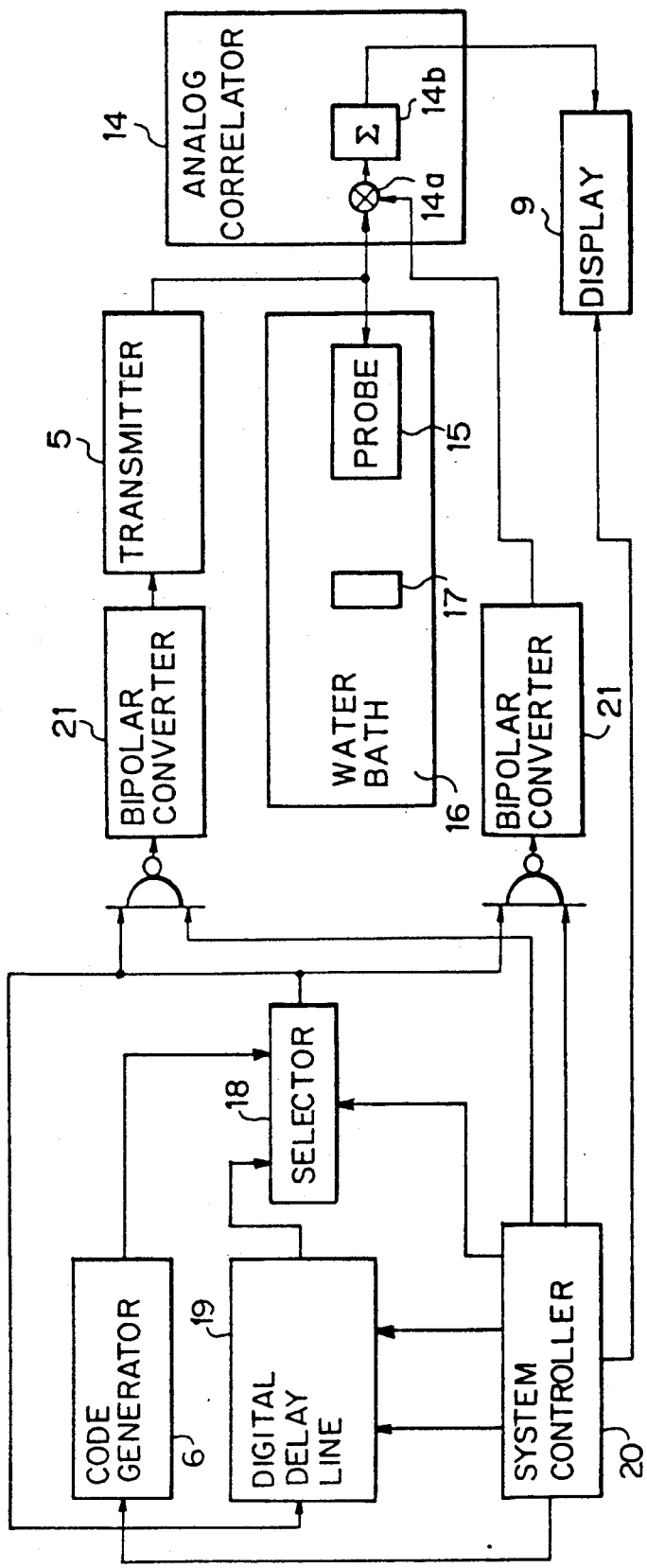
FIG. 3 is a constitutional diagram of the ultrasonic inspecting apparatus according to the prior art.
Figure 4:
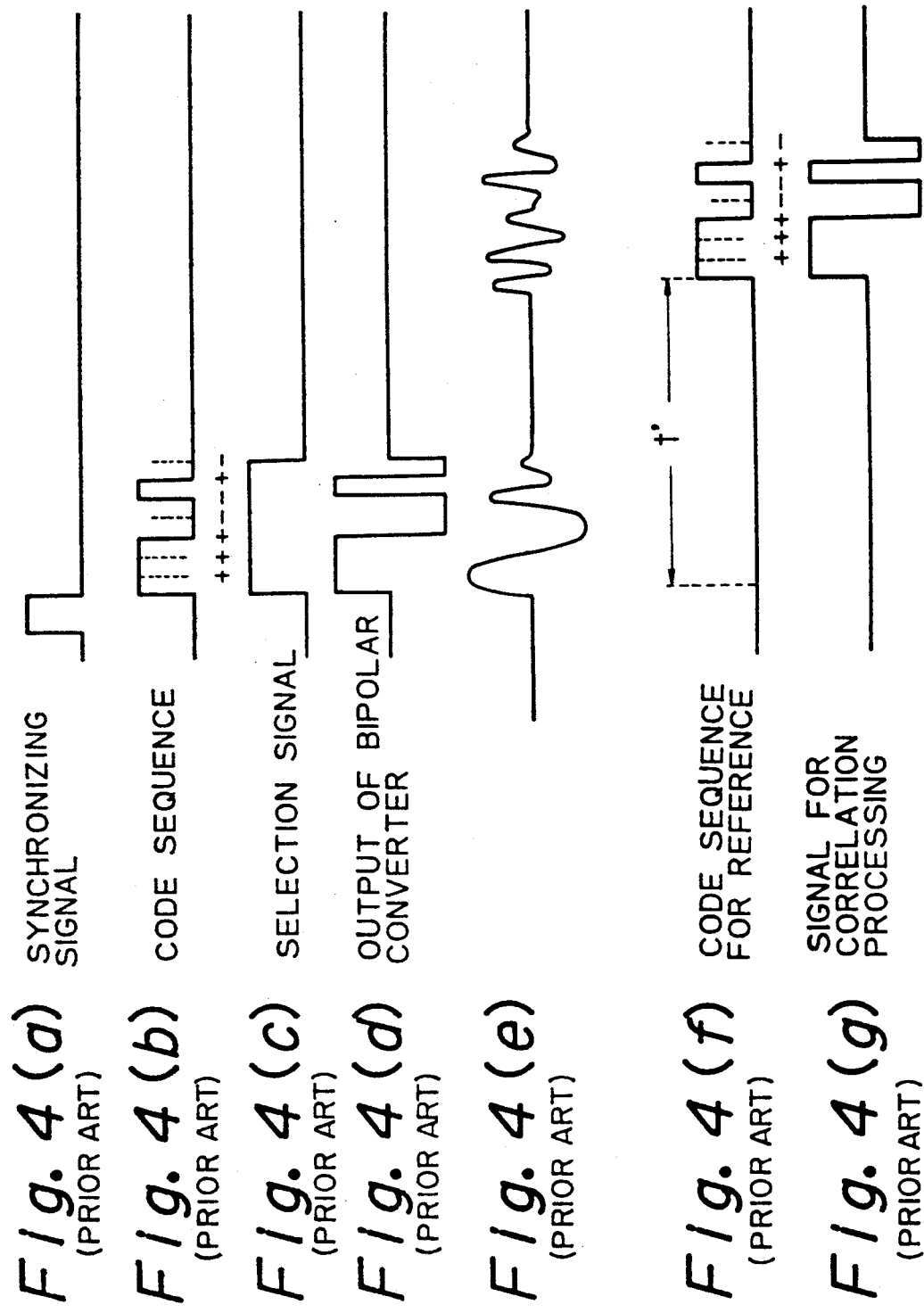
FIGS. 4(a), (b), (c), (d), (e), (f) and (g) are explanatory diagrams for operation of the apparatus in FIG. 3.

Incidentally, the sequences noted below are two Barker sequences having the same autocorrelation function shown in FIG. 1(b).

$a1_j = + + + - - + -$ $a2_j = + - + + - - -$

Figure 13:
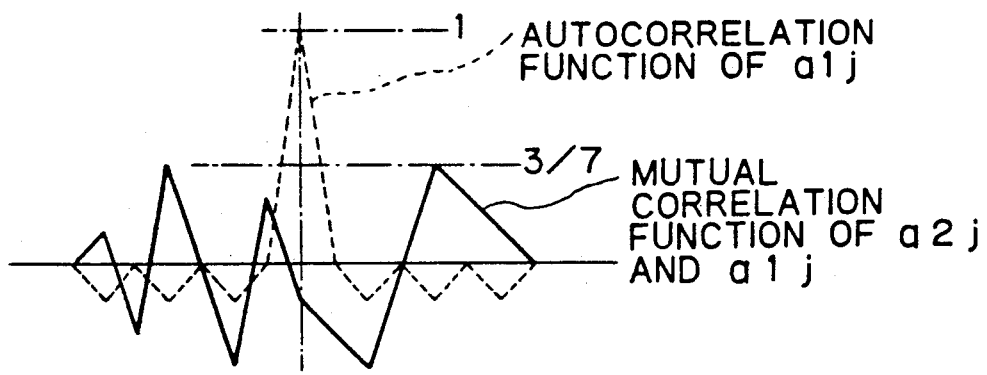
FIGS. 13(a) and (b) are explanatory diagrams with regard to the effect by the second embodiment of the present invention.
Figure 13:
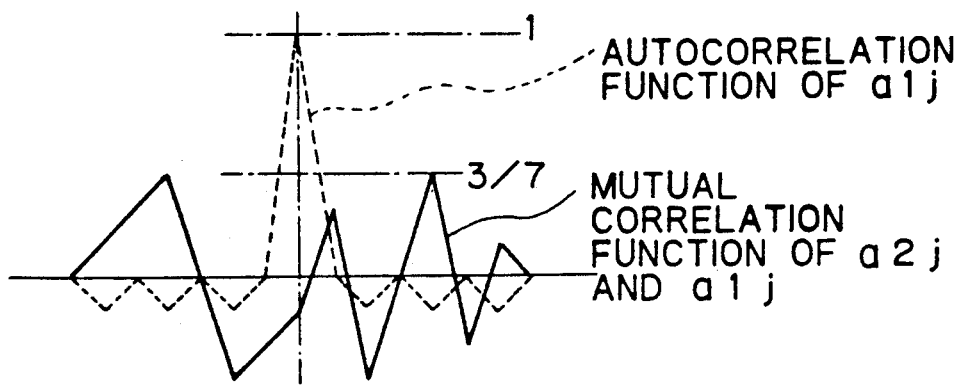

FIG. 13 are the results of the cross-correlation operations of the sequences $a1_j$ and $a2_j$ wherein FIG. 13(a) is the result of the operation for the sequence $a1_j$ using the sequence a2$_j$ as the reference signal and FIG. 13(b) is the result of the operation for the sequence a2$_j$ using the sequence a1$_j$ as the reference signal. As can be seen from these drawings, there will be no high peaks in the cross-correlation between the different sequences even though they have the same autocorrelation function.

It is to be noted that the problem regarding the reverberation echo is a phenomenon that the ultrasonic signal generated in the previous transmission cycle causes interference. An operation of the ultrasonic inspecting apparatus is explained in which the above problem is solved.

FIG. 14 illustrates a constitution of the code sequence controller and the polarity changer for transducer added to the apparatus shown in FIG. 8. In FIG. 14, numerals 1, 2, 3, 4, 5, 6, 7, 8 and 9 are identical to those shown in FIG. 8. Numeral 10 designates the code sequence controller adapted to switch the code sequence generated by the code generator 6 by use of the synchronous signals from the synchronous timing generation section 7 to any one of more than two different code sequences having an identical autocorrelation function as described above in the sequence of the transmission signal repetition period. Numeral 11 designates the transducer polarity changer having a function of changing the polarities of the ultrasonic signals input from the respective transducers 2 for reception in accordance with the instruction from the code sequence controller.

FIG. 15 is an explanatory diagram for operation of the apparatus shown in FIG. 14. FIG. 15(a) illustrates more than two different code sequences for transmission having identical autocorrelation function to be selected by the code sequence controller 10. FIG. 15(b) illustrates the reception wave forms in the case of the transmission code sequence being different from the code sequence of the transducer polarity changer 11.

Under control of the code sequence controller 10, the code generator 6 is adapted to alternately generate the code sequences shown in FIG. 15(a) (1) and (2) for each transmission signal repetition period. Concurrently, the transducer polarity changer 11 is also caused to change the polarities of the transducers for reception in the following manner.

[+ − + +] in case of the transmission sequence A of
[+ + − +]
[+ + + −] in case of the transmission sequence B of
[− + + +]

It is conceivable in the case of reverberation echo that the signals having the code sequence A becomes mixed in the transducers having a polarity corresponding to the code sequence B or the signals having the code sequence B becomes mixed in the transducers having a polarity corresponding to the code sequence A.

FIG. 15(b) illustrates the consequence when the transmission sequence B is mixed up in reception corresponding to the sequence A, due to reverberation echoes. The reception signals which have been converted to electric signals by the respective transducers 2-$_1$-2-$_4$ for reception are displaced as shown in FIG. 15(b) (1) through FIG. 15(b) (4) by the delay time T in the same manner as said operation of reception. FIG. 15(b) (5) illustrates the result of the reception wave form which is the sum of FIG. 15(b) (1), (2), (3) and (4) and is the comprehensive reception wave form eventually to be input to the reception amplifying section 8. Here, only the polarity is shown also.

FIG. 15(c) illustrates a consequence in which transmission sequence A is mixed up in reception corresponding to the sequence B, which is another case of the reverberation echoes. The reception signals which have been converted to electric signals by the respective transducers 2-$_1$-2-$_4$ for reception are shown in FIG. 15(c) (1)-(4), respectively. FIG. 15(c) (5) illustrates the result of the reception wave form which is the sum of FIG. 15(c) (1), (2), (3) and (4) and is the comprehensive reception wave form to be eventually input to the reception amplifying section 8.

According to the results shown in FIGS. 15(b) and (c), the echoes which have been encoded in the previous transmission period are caused to be reduced by approximately 6 dB. It is also to be noted that when other code sequences (the number of the sequences is seven) are also similarly processed the echoes which have been encoded in the previous transmission are caused to be reduced by approximately 7.4 dB as can be seen in FIG. 13.

As explained above, according to the second embodiment of the present invention, more than two different code sequences having an identical sharp autocorrelation function are repeatedly and serially switched for use for each cycle, such that the interference echoes such as reverberation echoes caused by the previous transmission signals may be reduced.

Furthermore, if such signals which correspond to the frequency response characteristics of the transducers 1 for transmission and the transducers 2 for reception are established in the transmission signals, the transmission energy may be effectively converted to the ultrasonic waves, so that S/N ratio may be enhanced as already explained.

The third embodiment of the present invention will next be explained.

Incidentally, the Barker sequence explained hereinabove possesses a sharp autocorrelation function; however, as seen from FIG. 1(b), it has sidelobe levels of 1/n. Therefore, classification of a flaw echo adjacent to a large bottom echo in a vertical flaw detection system is problematic. In such a case as above, it is possible to cope with the problem of sidelobes by using a complementary sequence. It has been considered that there is only one way of using the sum of two sequences which compose a complementary sequence in order to cancel sidelobes; however, the inventors have discovered that the sum of more than four kinds of autocorrelation functions such as $\rho_{aa}(k)$, $\rho_{bb}(k)$, $\rho_{cc}(k)$ and $\rho_{dd}(k)$, i.e.

$$\rho(k) = \rho_{aa}(k) + \rho_{bb}(k) + \rho_{cc}(k) + \rho_{dd}(k) \tag{8}$$

becomes zero at all points other than at k=0. Since this matter has not been referred to in the literature available heretofore, these sequences $\{a_j\}$, $\{b_j\}$, $\{c_j\}$ and $\{d_j\}$ are referred to, in this description, as a multiple complementary sequence or n-complementary sequence. The term "multiple complementary sequence" or "n-complementary sequence" used herein means sequences that comprises an even number (4 or more than 4) of sequences each having the same length and a range sidelobe which completely disappears when the respective autocorrelation functions of the sequences are summed. The inventors have discovered that such sequences exist. FIG. 16(a) shows an example of multiple complementary sequence expressed by the equation (9) wherein n=4.

$$\{a_j\} = --++$$
$$\{b_j\} = -+-+$$
$$\{c_j\} = -++-$$
$$\{d_j\} = ++++$$
(9)

FIG. 16(b) shows respective autocorrelation functions of $\{a_j\}$, $\{b_j\}$, $\{c_j\}$ and $\{d_j\}$ calculated based on the equation (3) in the range of $-n \leq k \leq n$.

FIG. 16(c) shows the sum $\rho(k)$ of the respective autocorrelation functions calculated based on the equation (8). As seen from this drawing, it is theoretically possible to make the levels of range sidelobes zero in the multiple complementary sequence. This is explained more elaborately later.

FIG. 17 illustrates a constitution of the third embodiment of the present invention. In FIG. 17, numerals 1, 2, 3, 4, 5, 6, 7, 8, 9, 10 and 11 are identical to those shown in FIG. 14. Numeral 12 designates the previous wave form storage section comprising, for example, and A/D converter, a digital memory and the like which are connected to the reception amplifier 8 and are adapted to store the flaw inspecting wave froms and output the previous flaw inspecting wave forms. Numeral 13 designates an adder comprising, for example, a digital adder and the like and adapted to add the previous flaw inspecting wave forms output from the previous wave form storage section and the present flaw inspecting wave forms output from the reception amplifier.

Figure 18D:
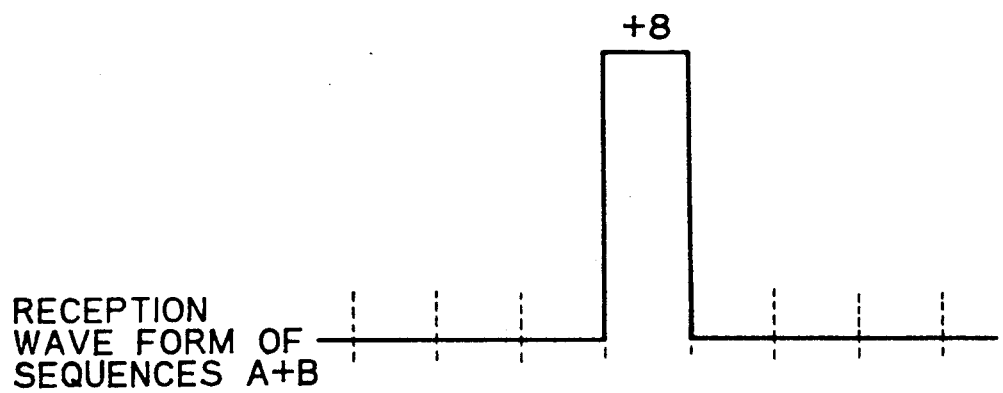
FIGS. 18(a), (b) and (c) are explanatory views of the apparatus shown in FIG. 17.

FIG. 18 is an explanatory diagram for operation of the apparatus shown in FIG. 17, and explains operation when a complementary sequence, or $n=2$ is used. FIG. 18(a) illustrates the code sequences A and B in the case of a complementary sequence. FIG. 18(b) illustrates reception wave forms of the transducers for reception in the case of sequence A and the comprehensive reception wave form. FIG. 18(c) illustrates reception wave forms of the transducers for reception in the case of sequence B and the comprehensive wave form. FIG. 18(d) illustrates the resultant wave forms by adding the comprehensive reception wave forms in the cases of sequence A and sequence B.

The code generator 6 under control of the code sequence controller 10 is adapted to transmit a complementary sequence or n-complementary sequence repeatedly and serially switch them to be amplified by the transmission section 5 and added to the transducer 1 for transmission. FIG. 18(a) illustrates the complementary sequence to be used in this instance. In the case of a complementary sequence, two kinds of sequences A, B are used.

As explained before, the ultrasonic signals which have passed through the object to be inspected are returned to the transducer 2 for reception. The reception signals output from the respective transducers 2 for reception are caused to pass through the transducer polarity changer which is concurrently controlled by the code sequence controller 10 and then transformed to the wave forms shown in FIG. 18(b) in case of the sequence A and those shown in FIG. 18(c) in case of the sequence B and then inputted to the reception amplification section. Those ultrasonic signals thus amplified by the reception amplification section 8 are stored in the previous wave form storage section 12, and fed at the same time to the adder 13. The adder 13 is adapted to synchronously read out the ultrasonic signals having different code sequences received by the previous wave form storage section 12 and add the previous flaw inspecting wave forms thus read out and the flaw inspecting wave forms at present. This operation executes the function of adding the wave forms shown in FIG. 18(b) (5) and FIG. 18(c) (5). The result of the operation is shown in FIG. 18(d).

The above is mentioned with respect to the case of using a complementary sequence ($n=2$). It is easy to apply the above to the case of using multiple complementary sequence ($n \geq 4$).

The use of a complementary sequence or n-complementary sequence having the above described features surely improves the range sidelobes as well as provides further characteristic advantage. For example, if an outside electric noise of a fairly high level while having nocorrelation with the sequences is intermixed therewith, the noise may be reduced to the level determined by the sequence length N, but, in some cases, a sufficient S/N ratio may not be attained. In such a case, if the advantageous feature of utilizing the summed result with respect to a number of sequences is employed, a further effect is achieved such that the outcoming electric noise can be further reduced to the level determined by 2 in the case of using a complementary sequence in flaw detection and to a level determined by 4 in the case of using the n-complementary sequence shown in FIG. 16, and to a level determined by n in the case of using the n-complementary series in general, and also, range sidelobes are reduced. Incidentally, while similar effects can be expected by use of a mere averaging process, the use of sequences with respectively different autocorrelation functions theoretically achieves a further advantageous effect in that it can also reduce the outside electrical noise having a periodicity feature.

According to the third embodiment of the present invention, as explained above, more than two code sequences are used so that the result of adding the respective autocorrelation function will be zero except at the peak. Consequently, the range sidelobes may be improved and the level of incoming noise be further reduced, as the number of code sequences increases.

Furthermore, if the signals having frequency characteristics corresponding to the frequency response characteristics of the transducers 1 for transmission and the transducers 2 for reception are established in the transmission signals, the transmission energy may be effectively converted to ultrasonic waves, thereby the S/N ratio may be further enhanced as already explained.

The present invention achieves, as explained above, improvements of S/N ratios by enhancement of flaw detection signals and/or reduction of noise and incidental undesired signals received from outside. The present invention will now be further explained with regard to the case where a specimen exhibiting a large ultrasonic wave attenuation, such as stainless steel and/or cast iron is analyzed.

Figure 19:
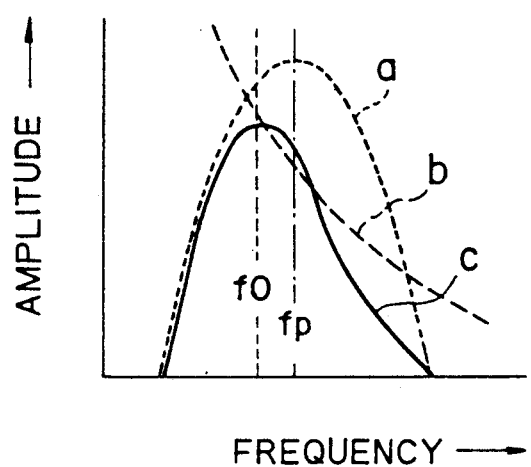
FIG. 19 is an explanatory view with regard to another effect of the third embodiment of the present invention.

The graph shown in FIG. 19 illustrates a frequency response characteristic a of the ultrasonic probe, a frequency response characteristic b of the specimen and a combined frequency response characteristic c. In the foregoing, explanation has been made on the basis that an energy transmitting efficiency is made maximum by matching the transmission signal generated at the code generator 6, as shown in FIG. 12, to the center frequency $f_p$ of the probe. However, in the instant example where the attenuation within the specimen is to be considered, there may be a case in which the frequencies providing maximum efficiency are not matched due to the attenuation (frequency response characteristic) of the specimen to the central frequency of the probe. In a case such as the above, transmission signal energy can be more efficiently directed to the body of the specimen to improve an S/N ratio of the receiving signal if a frequency of the transmission signal generated at the code generator 6 is not matched with the central frequency ($f_p$) of the probe but is matched with the central frequency ($f_o$) of the frequency response characteristic of the combination of the probe and specimen.

It is to be noted that the present invention is applied in an ultrasonic inspecting apparatus to improve the S/N ratio of the reception signals in the course of inspecting flaws in an inspection object depending on the level of the reflected echo. The present invention may also be applied for the inspection or measurement of a beam path length to the reflector and the bottom surface for the purpose of measuring the beam path length to the flaws of an object or the thickness of an object. When the present invention is applied in such cases as described above, it is possible to prevent an erroneous inspection of the locations of the flaws in the object caused by incoming external noise by exaggerating the signals in question and reducing the external noises.

According to the present embodiment, although the transducers 1 for transmission and the transducers 2 for reception constitute separate units, a similar effect to the one provided by the present invention may naturally be attained if one of the transducers for reception is shared with the transducer 1 for transmission.

What is claimed is:

1. An ultransonic inspecting apparatus characterized by comprising:
   a sequence generating means for generating a finite sequence with a lenght N which is composed of binary values and has a sharp autocorrelation function, the sequence generating means generating the finite sequence by changing between the binary values per each unit time T;
   a transmission signal generating means for generating a transmission signal corresponding to the sequence;
   a transmitting means for transmitting ultrasonic waves to an object by means of said transmission signal;
   a receiving means for receiving an echo corresponding to said transmission signal, the receiving means having N number of transducers each of which is placed over the other so that each ultrasonic propagation time between them is identical to the unit time T and a series of polarities of outputs of the transducers correspond to a series of binary values which is obtained by reversing the time order of the binary values of the sequence; and
   a means for generating the sum of the outputs of the transducers.

2. An ultrasonic inspecting apparatus characterized by comprising:
   a sequence generating means for generating a finite sequence with a length N which is composed of binary values and has a sharp autocorrelation function, the sequence generating means generating the finite sequence by changing between the binary values per each unit time T;
   a sequence switching means for switching each sequence generated by the sequence generating means between two or more finite sequences in turn per each transmission repeating period, each sequence having an autocorrelation function almost identical with the other;
   a transmission signal generating means for generating a transmission signal corresponding to the sequence generated by the sequence generating means;
   a transmitting means for transmitting ultrasonic waves to an object by means of said transmission signal;
   a receiving means for receiving an echo corresponding to said transmission signal, the receiving means having N number of transducers each of which is placed over the other so that each ultrasonic propagation time between them is identical to the unit time T;
   a selecting means for selectively inverting or not inverting the polarity of the output of each of the transducers so that the series of the polarities of outputs corresponds to a series of the binary values which is obtained by reversing the time order of the binary values of the sequence generated by the sequence generating means; and
   a means for generating the sum of the outputs of the transducers.

3. An ultrasonic inspecting apparatus characterized by comprising:
   a sequence generating means for generating a finite sequence with a length N which is composed of binary values and has a sharp autocorrelation function, the sequence generating means generating the finite sequence by changing between the binary values per each unit time T;
   a sequence switching means for switching each sequence generated by the sequence generating means between two or more finite sequences in turn per each transmission repeating period, the sequences having a characteristic that the sum of their autocorrelation functions becomes "0" at all points excluding the peak point;
   a transmission signal generating means for generating a transmission signal corresponding to the sequence generated by the sequence generating means;
   a transmitting means for transmitting ultrasonic waves to an object by means of said transmission signal;
   a receiving means for receiving an echo corresponding to said transmission signal, the receiving means having N number of transducers each of which is placed over the other so that each ultrasonic propagation time between them is identical to the unit time T;
   a selecting means for selectively inverting or not inverting the polarity of the output of each of the transducers so that the series of the polarities of outputs corresponds to a series of the binary values which is obtained by reversing the time order of the binary values of the sequence generated by the sequence generating means;
   a means for generating the sum of the outputs of the transducers;
   a memory means for storing the sum; and
   an adding means for adding the sums each of which is obtained in each transmission period.

4. An ultrasonic inspecting apparatus according to claim 1, 2 or 3, wherein said transmission signal generating means comprises a wave form generating means for generating a transmission signal with a wave form having a frequency component $f_o$ within a unit time T and changed with respect to its phase by 180° in accordance with the binary values of the codes.

5. An ultrasonic inspecting apparatus according to claims 2 or 3, wherein the number of the sequences switched by the switching means is four or more than four.

* * * * *

UNITED STATES PATENT AND TRADEMARK OFFICE
CERTIFICATE OF CORRECTION

PATENT NO. : 5,065,629

DATED : November 19, 1991

INVENTOR(S) : Mitsuhiro Koike, et al

It is certified that error appears in the above-identified patent and that said Letters Patent is hereby corrected as shown below:

On the title page: Item [54] Title:

ULTRASONIC INSPECTING APPARATUS

Signed and Sealed this

Thirteenth Day of July, 1993

Attest:

MICHAEL K. KIRK

*Attesting Officer*     Acting Commissioner of Patents and Trademarks